(12) United States Patent
Shigemori et al.

(10) Patent No.: US 6,849,410 B2
(45) Date of Patent: Feb. 1, 2005

(54) METHOD FOR DETECTING DNA POLYMORPHISM APPLYING TRIPLE STRAND DNA FORMATION TECHNIQUE

(75) Inventors: Yasushi Shigemori, Chiba (JP); Michio Oishi, Chiba (JP); Osamu Ohara, Chiba (JP)

(73) Assignees: Aisin Cosmos R & D Co., Ltd., Kariya (JP); Kazusa DNA Research Institute Foundation, Kisarazu (JP)

(*) Notice: Subject to any disclaimer, the term of this patent is extended or adjusted under 35 U.S.C. 154(b) by 0 days.

(21) Appl. No.: 09/989,526

(22) Filed: Nov. 21, 2001

(65) Prior Publication Data

US 2003/0017475 A1 Jan. 23, 2003

(30) Foreign Application Priority Data

Dec. 20, 2000 (JP) ........................................ 2000-386361

(51) Int. Cl.⁷ ........................... C12Q 1/68; C07H 21/02; C07H 21/04
(52) U.S. Cl. ........................... 435/6; 536/23.1; 536/24.3
(58) Field of Search ................................ 435/6, 91.1, 4; 536/23.1, 24.3; 530/350

(56) References Cited

U.S. PATENT DOCUMENTS

| | | | | |
|---|---|---|---|---|
| 5,948,653 A | * | 9/1999 | Pati et al. .................... | 435/6 |
| 6,074,853 A | * | 6/2000 | Pati et al. .................... | 435/91.1 |
| 6,200,812 B1 | * | 3/2001 | Pati et al. .................... | 435/463 |
| 6,335,164 B1 | * | 1/2002 | Kigawa et al. ................ | 435/6 |
| 6,541,226 B1 | | 4/2003 | Shigemori et al. | |
| 2003/0113716 A1 | * | 6/2003 | Erikson et al. ................ | 435/6 |

FOREIGN PATENT DOCUMENTS

EP    1 065 279 A1    1/2001

* cited by examiner

Primary Examiner—Jeffrey Fredman
Assistant Examiner—Teresa E Strzelecka
(74) Attorney, Agent, or Firm—Burns, Doane, Swecker & Mathis, L.L.P.

(57) ABSTRACT

An objective of this invention is to provide a method for detecting DNA polymorphism that has high sensitivity and efficiency and does not need long DNA searching region.

A homologous recombination protein RecA makes partial triple strand DNA from target double DNA and oligonucleotide probe complementary to the DNA. The triple strand DNA maintains stable triple strand DNA after RecA protein is removed. The present inventors found that the thermostability of triple strand DNA changes greatly when there is a mismatch between target DNA and oligonucleotide probe because of the existence of polymorphism in the target DNA. Utilizing this change of thermostability, efficient detection of polymorphism in labeled DNA is possible by examining whether oligonucleotide probe is released and the triple strand DNA is solved after heat treatment of triple strand DNA formed using homologous recombination protein.

8 Claims, 14 Drawing Sheets

FIG. 3A
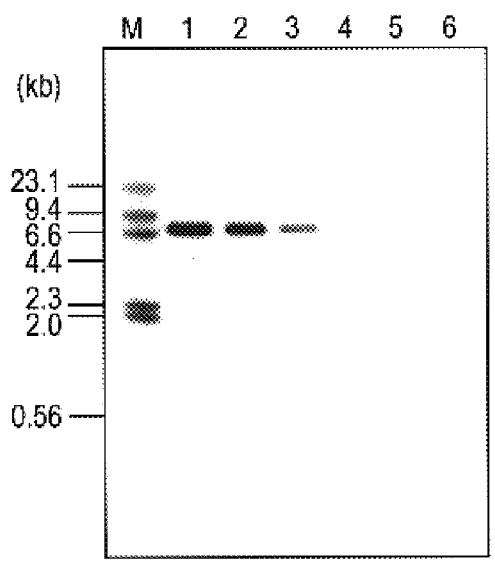
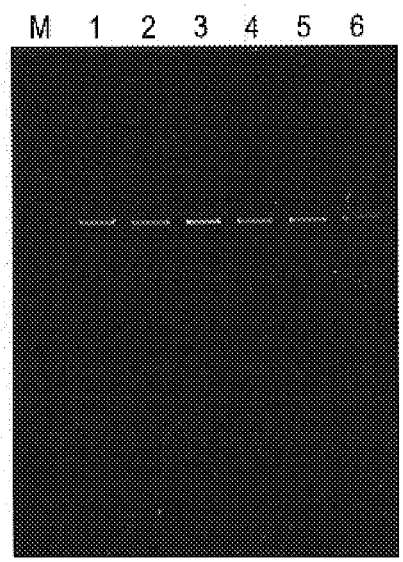
FIG. 3B
FIG. 3C

METHOD FOR DETECTING DNA POLYMORPHISM APPLYING TRIPLE STRAND DNA FORMATION TECHNIQUE

FIELD OF THE INVENTION

The present invention relates to a method for detecting a DNA polymorphism using a homologous recombination protein.

BACKGROUND OF THE INVENTION

Differences in various phenotypes of humans, including disease, are known to be derived from the differences in DNA nucleotide sequence in an individual genome. This difference is called single nucleotide polymorphism (SNP). SNPs are found widely in human genome of about 3 billion base pairs and the total number of SNPs is not less than 3 millions. Thus, SNPs can be the DNA markers having exceptionally higher density that known DNA markers such as RFLP (restriction fragment length polymorphism) and STR (microsatellite), which are conventional DNA markers. Therefore, high-precision analysis, which has been impossible using conventional DNA markers, is possible by using SNPs, and it is hoped that SNP can be applied to detection of disease genes, determination of disease sensitivity, and development of pharmaceutical.

Known methods for detecting DNA polymorphism including SNP are as follows:

(1) PCR-SSCP (Single-strand Conformation Polymorphism)

When double strand DNA fragment amplified by PCR is separated by electrophoresis, its electrophoretic mobility is proportionate to the size of the DNA molecule. When single strand DNA molecule is electrophoresed with gel including denaturant, its electrophoretic mobility is proportional to the size of the molecule. When it is electrophoresed without denaturant, single strand DNA forms folded structure (higher order structure) due to intramolecular interaction. Thus, electrophoretic mobility of the DNA forming such folded structure varies depending on its structure. In the PCR-SSCP method, double strand DNA amplified by PCR is denatured by heat or alkaline treatment. Then, the single strand DNA obtained is electrophoresed with polyacrylamide gel without denaturant. The single strand DNA is folded due to intramolecular interaction and forms higher order structure. The interaction of the folded structure can vary depending on the difference of nucleotide. The difference can be detected by staining the DNA fragment electrophoresed. Ethidium bromide widely used for the detection of DNA stains double strand DNA, but it does not stain single strand DNA usually. Therefore, silver staining is applied in this method.

However, there is a problem with this technique because the region for searching is from 200 to 300 bp and the detection fails when the region is not more than that.

(2) Direct Sequencing

A direct sequencing method is the method in which nucleotide sequence is determined directly using DNA amplified by PCR as a template without subcloning with vector. This method can remove misreading which is a drawback of PCR. As misreading of PCR is said to occur once over 400 bp, one nucleotide substitution per 400 nucleotides should be detected after subcloning. However, because errors in nucleotide sequence introduced randomly are diluted into 1/400 on an average, they mostly can be ignored in the direct sequencing method. In this method, after amplifying DNA strand by primary PCR, secondary PCR called asymmetric PCR that amplifies single strand DNA is performed. Then, the nucleotide sequence is generally determined using dideoxy method. This secondary PCR amplifies single strand DNA by conducting PCR using a pair of primers in which limited amount of one primer is used (1:10~1:100, usually).

Because this method needs to sequence genes one after another, the probability to find the mutation is low. Also, the mutation can be missed because of the problem of sequencer.

(3) IGCR (In-gel Competitive Reassociation) Method

There is the method using competitive reassociation of DNA in gel as a method for cloning DNA having slightly different structure. Using reference DNA dephosphorylated, DNA is denatured in electrophoresis gel, reassociated, recovered, and cloned so that the target DNA fragment having changed structure is selectively concentrated.

However, this technique is searching for longer region than that in PCR-SSCP method. It has problems in which, for example, it cannot detect repetitive sequence because of its mechanism.

Therefore, it was hoped to develop efficient and certain method for detecting polymorphism that does not require long DNA region for searching.

SUMMARY OF THE INVENTION

The present invention was done in view of above-mentioned situation. An objective of this invention is to offer new method for detecting DNA polymorphism having high sensitivity and efficiency, in which long DNA region for searching is not required.

The present inventors have intensively been studying homologous recombination of DNA in vivo. As a result of the study, the present inventors revealed that E coli RecA protein involved in homologous recombination can make triple strand DNA without long homologous region and that the triple strand DNA becomes unstable by heat when a pair of mismatch exists in one double strand DNA among triple strand DNA. Then, the present inventors reminded a following method for detecting DNA polymorphism. First, an oligonucleotide probe complementary to one strand of test DNA region to examine is prepared and hybridized to the test DNA region using a homologous recombination protein. After the formation of triple strand DNA in the test DNA region, the homologous recombination protein is removed. When polymorphism exists in the test DNA region, mismatch nucleotide pair occurs between the oligonucleotide probe and one strand of the test DNA region which makes the structure of triple strand DNA unstable to heat compared to the test DNA region in which no polymorphism exists. If the triple strand DNA is treated with heat, the oligonucleotide probe is released from unstable triple strand DNA in which mismatch exists. Therefore, the present inventors considered that the existence of polymorphism in test DNA region could be detected by detecting oligonucleotide probe hybridized to the test DNA region.

The present inventors investigated whether the detection of DNA polymorphism was actually possible by using the above-mentioned method. At first, the present inventors examined the condition in which a test DNA region including polymorphism and an oligonucleotide which was a probe for the detection of polymorphism could form stable triple strand DNA through a homologous recombination protein. As a result, it was revealed that triple strand DNA could be formed if the length of the oligonucleotide probe was not less than 40 nucleotides. Next, the present inventors examined the stability of triple strand DNA, which comprises an oligonucleotide completely complementary to one strand of a test DNA region or an oligonucleotide including one mismatch and the test double DNA, to heat. As a result, the triple strand DNA formed when the completely complementary oligonucleotide was more stable than that containing an oligonucleotide including one mismatch. Thus, the difference of thermostability between them was clear. It was revealed that the stability of the triple strand DNA was markedly affected by mismatch derived from even one nucleotide mutation in a DNA strand. Therefore, it is considered that the heat treatment of triple strand DNA makes oligonucleotide having mismatch release from target DNA and makes the structure of triple strand DNA collapse. Using the above-mentioned result, precise detection of polymorphism existing in the test DNA is possible by detecting oligonucleotide that forms triple strand DNA with target DNA even after heat treatment of the triple strand DNA that is formed using homologous recombination protein.

Because the length of DNA is 40 bp or more for the formation of triple strand DNA using homologous recombination protein, the long DNA region for test DNA is not necessary. Furthermore, the specificity for binding of probe and target DNA in triple strand DNA using homologous recombination protein is considered to be higher than that of probe and target DNA in general hybridization, the sensitivity for the detection of DNA polymorphism in the method described above is considered to be higher than that of other methods using known general hybridization.

The present inventors found a new method that could detect DNA polymorphism efficiently by using homologous recombination protein as described above and the present invention was completed.

The present invention relates to a new method which does not require long DNA region for searching and can detect DNA polymorphism with high specificity and efficiency. More specifically, the present invention provides the following:

[1] A method for detecting a DNA polymorphism in a double strand DNA, said method comprising the steps of (a) to (d) below:
  (a) contacting (i) a double strand DNA comprising a test polymorphic site, (ii) an oligonucleotide probe that hybridizes to a region comprising said polymorphic site in said double strand DNA, and (iii) a homologous recombination protein under reaction conditions where a triple strand DNA complex is formed,
  (b) removing the homologous recombination protein from the triple strand DNA complex formed in the step (a), thereby generating a triple strand DNA,
  (c) conducting heat treatment of the triple strand DNA generated by removing the homologous recombination protein, under conditions where the oligonucleotide probe is released from said triple strand DNA, when the test polymorphic site in the double strand DNA is not complementary to a corresponding site in said oligonucleotide probe,
  (d) detecting an oligonucleotide probe that binds to the double strand DNA to form the triple strand DNA,

[2] The method of [1], wherein the double strand DNA comprising a test polymorphic site has a DNA terminus,

[3] The method of [2], wherein the test polymorphic site is located within 20 bases from the DNA terminus,

[4] The method of [1], wherein the length of the oligonucleotide probe is from 20 to 120 bases,

[5] The method of [1], wherein the homologous recombination protein is a RecA protein from E. coli,

[6] The method of [1], wherein, in the step (a), a nucleotide triphosphate is added to the reaction system,

[7] The method of [1], wherein, in the step (b), the homologous recombination protein is removed by conducting protein degradation enzyme treatment,

[8] The method of [7], wherein the protein degradation enzyme is proteinase K,

[9] A lit for detecting a polymorphism in a double strand DNA comprising a test polymorphic site, said kit comprising the following components: (a) an oligonucleotide probe that hybridizes to the double strand DNA comprising the test polymorphic site and (b) a homologous recombination protein,

[10] A kit of [9], further comprising at least one selected from the group consisting of (i) a reagent removing the homologous recombination protein, (ii) nucleotide triphosphate, and (iii) a buffering agent.

BRIEF DESCRIPTION OF THE DRAWINGS

FIG. 1A schematically shows the relation of the position between target DNA used for the experiment and the oligonucleotide containing sequence complementary to the DNA.

FIG. 1B is the photograph of detecting the signal of labeled oligonucleotide that bound to the target DNA after triple strand DNA structure was electrophoresed.

FIG. 1C is the photograph of staining gel with ethidium bromide after electrophoresis. Each lane is as follows:

Lane M: DNA size marker (The left in the figure indicates size. This size marker is λDNA which was cut by restriction enzyme Hind III and whose 5'-terminal was labeled with $^{32}$P using T4 Polynucleotide kinase and [$\gamma$-$^{32}$P] ATP.

Lane 1: The reaction was performed using oligonucleotide 1 labeled with $^{32}$P adding RecA and ATP-γS.

Lane 2: The reaction was performed in the same manner of lane 1 in which RecA was not added.

Lane 3: The reaction was performed in the same manner of lane 1 in which ATP-γS was not added.

Lane 4: The reaction was performed in the same manner of lane 1 in which RecA and ATP-γS were not added.

Lane 5: The reaction was performed in the same manner of lane 1 in which oligonucleotide 2 labeled with $^{32}$P was used.

Lane 6: The reaction was performed in the same manner of lane 1 in which oligonucleotide 3 labeled with $^{32}$P was used.

Lane 7: The reaction was performed in the same manner of lane 1 in which pBR322 DNA cut by restriction enzyme ScaI was used as a target DNA and also oligonucleotide 3 labeled with $^{32}$P was used.

Figure 2A:
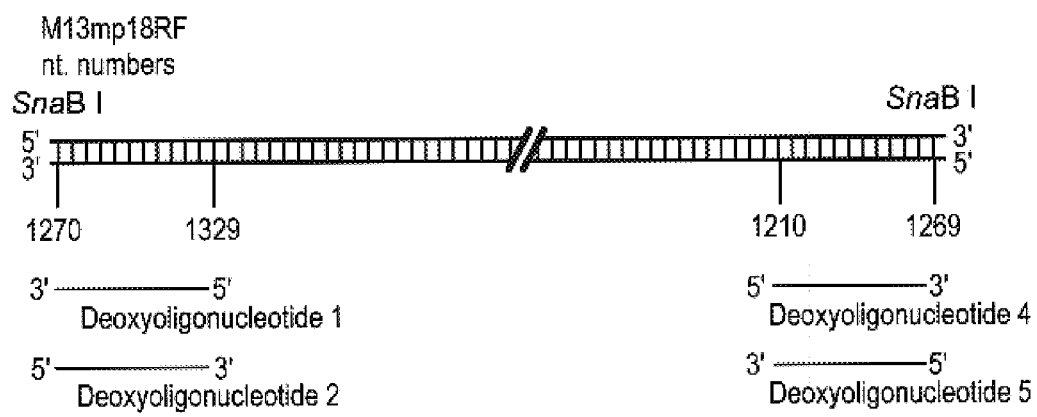
Figure 2B:
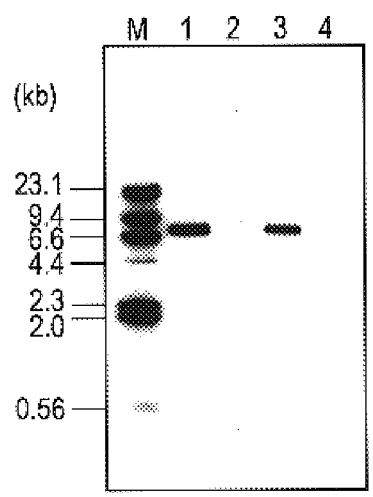
Figure 2C:
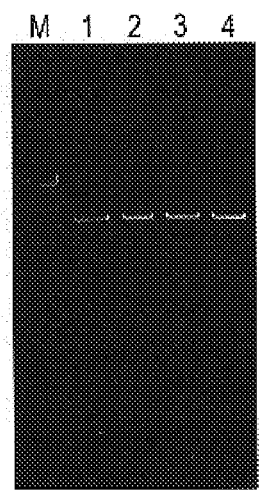

FIGS. 2A–2C show the following:

FIG. 2A schematically shows the relation of the position between target DNA used for the experiment and the oligonucleotide containing sequence complementary to the DNA.

FIG. 2B is the photograph of detecting the signal of labeled oligonucleotide that bound to the target DNA after triple strand DNA structure was electrophoresed.

Figure 1A:
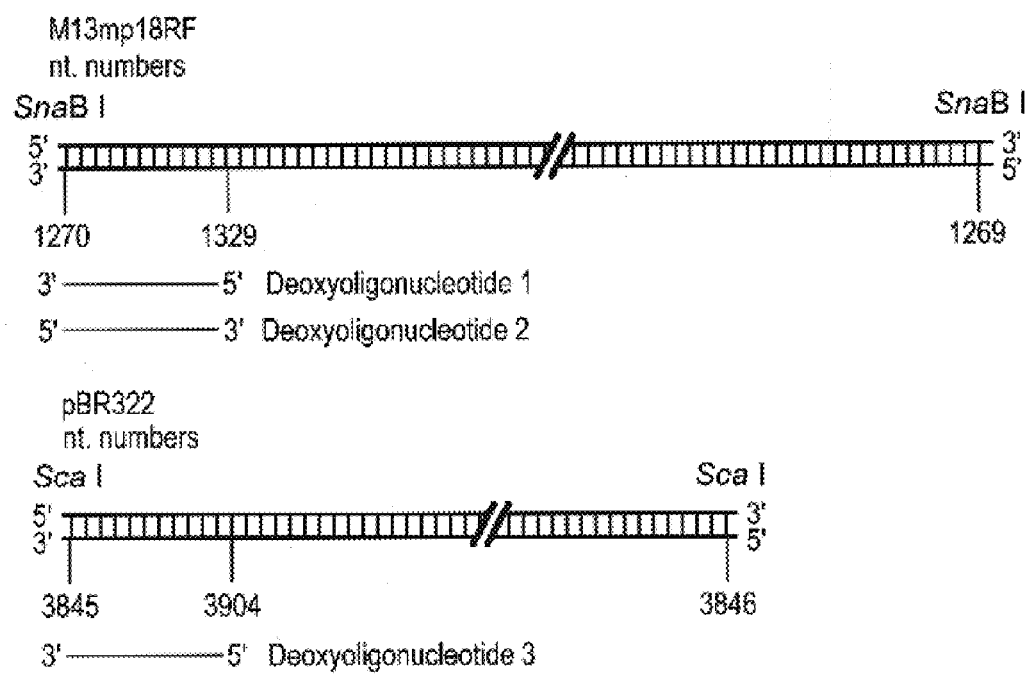
FIGS. 1A–1C show the following.
Figure 1B:
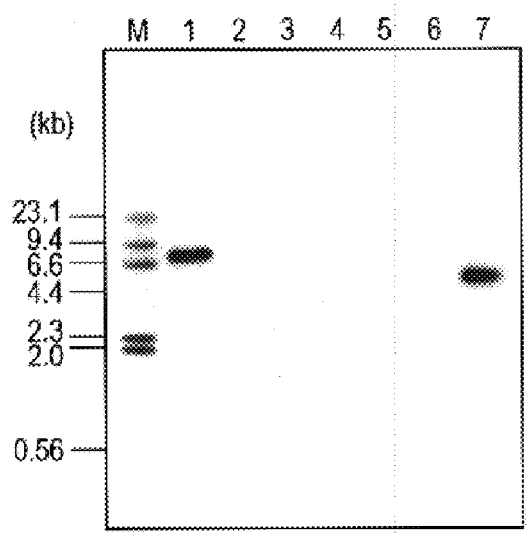

FIG. 2C is the photograph of staining gel with ethidium bromide after electrophoresis. Each lane is as follows:

Lane 1: The reaction was performed in the same manner of lane 1 of FIG. 1B.

Lane 2: The reaction was performed in the same manner of lane 1 in which oligonucleotide 2 labeled with $^{32}P$ was used.

Lane 3: The reaction was performed in the same manner of lane 1 in which oligonucleotide 4 labeled with $^{32}P$ was used.

Lane 4: The reaction was performed in the same manner of lane 1 in which oligonucleotide 5 labeled with $^{32}P$ was used.

FIGS. 3A–3C show the following:

FIG. 3A schematically shows the relation of the position between target DNA used for the experiment and the oligonucleotide containing sequence complementary to the DNA.

FIG. 3B is the photograph of detecting the signal of labeled oligonucleotide that bound to the target DNA after triple strand DNA structure was electrophoresed.

FIG. 3C is the photograph of staining gel with ethidium bromide after electrophoresis. Each lane is as follows:

Lane 1: The reaction was performed in the same manner of lane 1 of FIG. 1B.

Lane 2: The reaction was performed in the same manner of lane 1 in which oligonucleotide 6 that had the terminal sequence retaining terminal 10 bp nucleotides of the target DNA was used.

Lane 3: The reaction was performed in the same manner of lane 1 in which oligonucleotide 7 that had the terminal sequence retaining terminal 20 bp nucleotides of the target DNA was used.

Lane 4: The reaction was performed in the same manner of lane 1 in which oligonucleotide 8 that had the terminal sequence retaining terminal 30 bp nucleotides of the target DNA was used.

Lane 5: The reaction was performed in the same manner of lane 1 in which oligonucleotide 8 that had the terminal sequence retaining terminal 40 bp nucleotides of the target DNA was used.

Figure 4A:
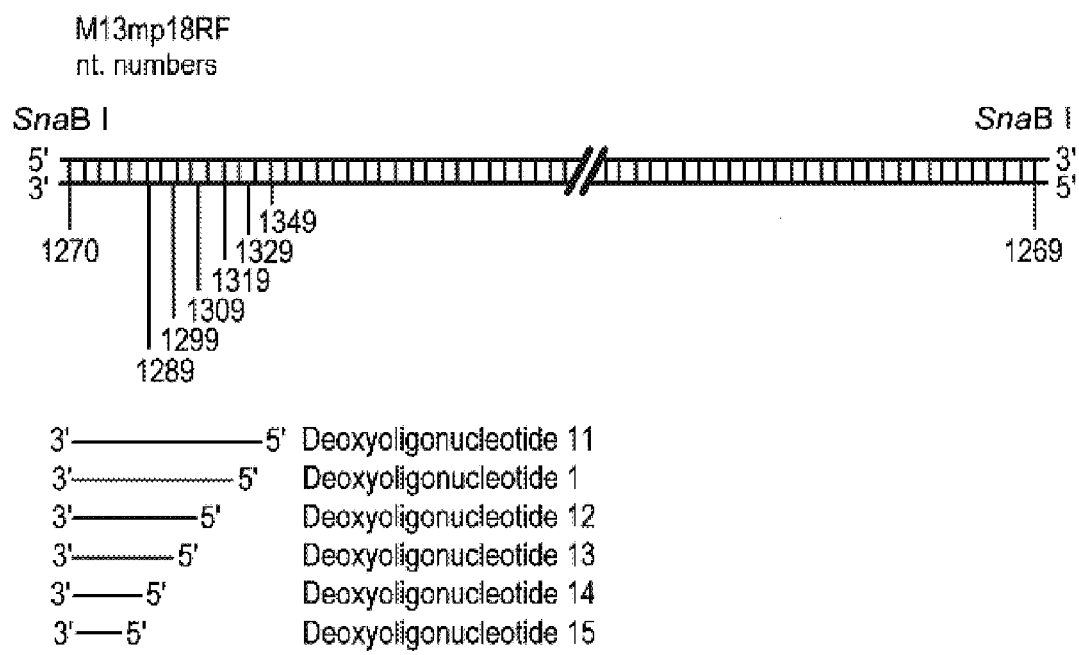
Figure 4B:
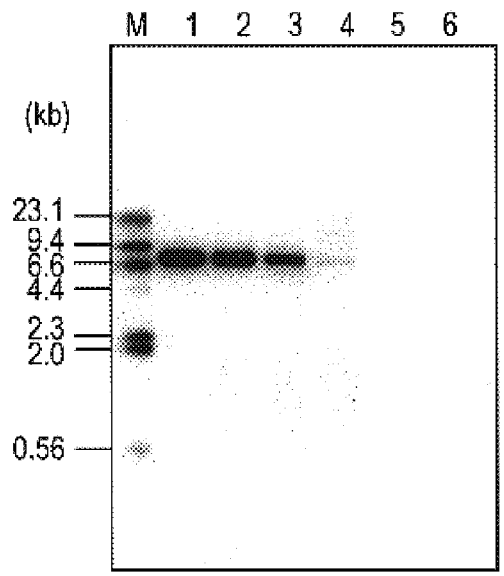
Figure 4C:
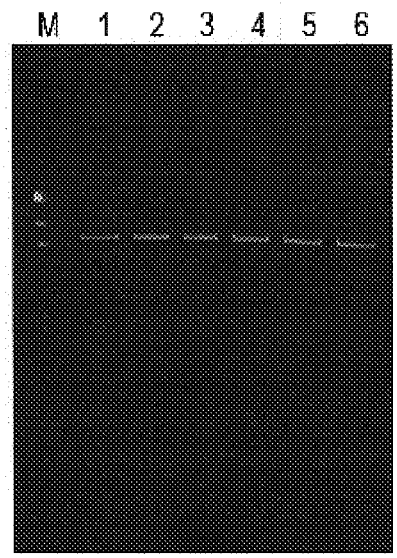

Lane 6: The reaction was performed in the same manner of lane 1 in which oligonucleotide 8 that had the terminal sequence retaining terminal 50 bp nucleotides of the target DNA was used;

FIGS. 4A–4C show the following:

FIG. 4A schematically shows the relation of the position between target DNA used for the experiment and the oligonucleotide containing sequence complementary to the DNA.

FIG. 4B is the photograph of detecting the signal of labeled oligonucleotide that bound to the target DNA after triple strand DNA structure was electrophoresed.

FIG. 4C is the photograph of staining gel with ethidium bromide after electrophoresis. Each lane is as follows:

Lane 1: The reaction was performed in the same manner of lane 1 of FIG. 1B in which labeled oligonucleotide 11 that had the 5'-terminal sequence extending 20 per of oligonucleotide 1 was used.

Lane 2: The reaction was performed in the same manner of lane 1 of FIG. 1(A) (oligonucleotide 1 was used).

Lane 3: The reaction was performed in the same manner of lane 1 in which labeled oligonucleotide 12 that was oligonucleotide 1 whose 5'-terminal 30 mer of was deleted.

Lane 4: The reaction was performed in the same manner of lane 1 in which labeled oligonucleotide 13 that was oligonucleotide 1 whose 5'-terminal 40 mer of was deleted.

Lane 5: The reaction was performed in the same manner of lane 1 in which labeled oligonucleotide 14 that was oligonucleotide 1 whose 5'-terminal 50 mer of was deleted.

Lane 6: The reaction was performed in the same manner of lane 1 in which labeled oligonucleotide 15 that was oligonucleotide 1 whose 5'-terminal 60 mer of was deleted FIG. 5: The principle of the detection in this invention is schematically shown.

Figure 6A:
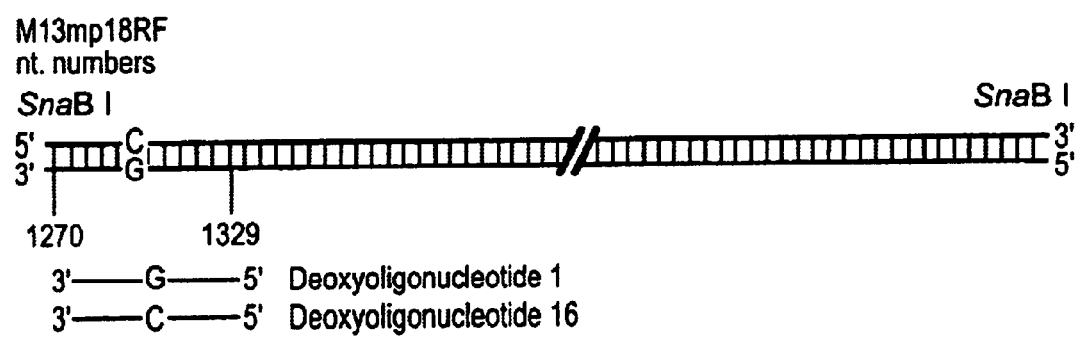
Figure 6B:
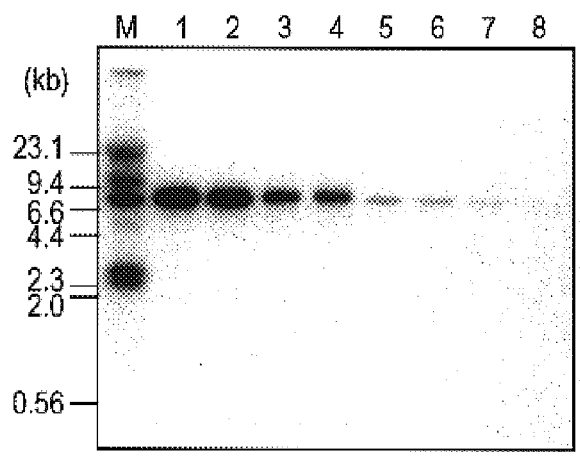
Figure 6B:
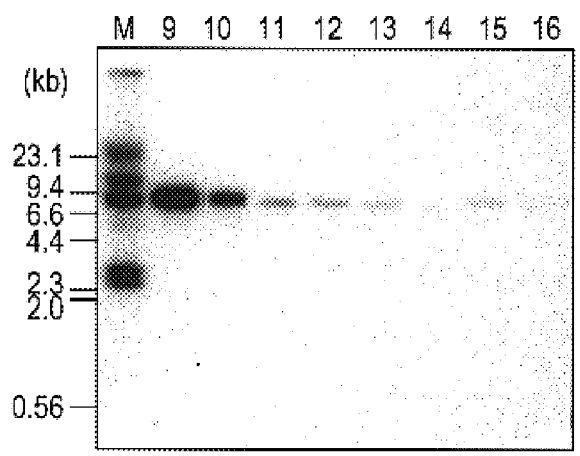
Figure 6B:
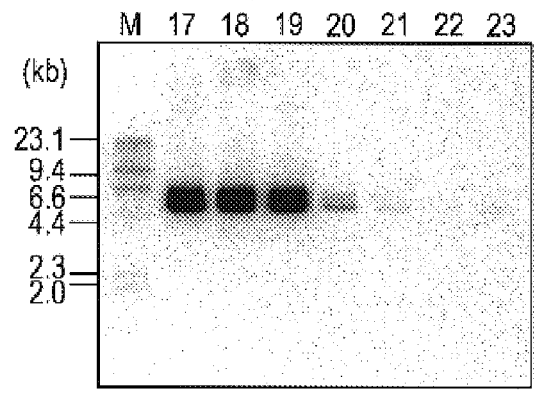
Figure 6C:
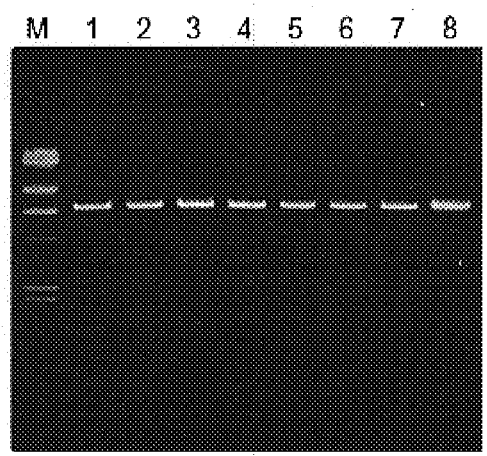
Figure 6C:
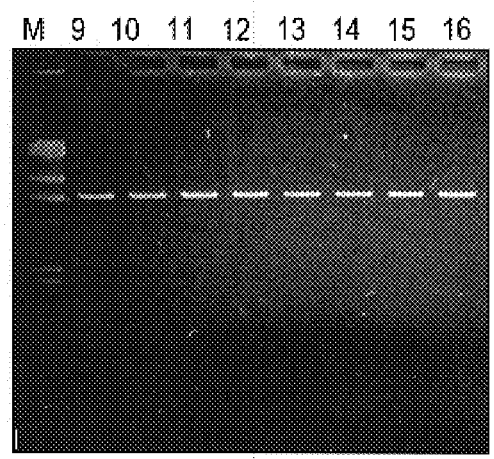
Figure 6C:
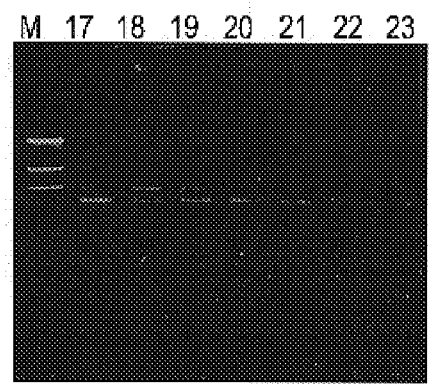

FIGS. 6A–6C show the following:

FIG. 6A schematically shows the relation of the position between target DNA used for the experiment and the oligonucleotide containing sequence complementary to the DNA. "G" or "C" on the oligonucleotide indicates the types of the nucleotide located at corresponding base pair of the target DNA shown just described above in character in the figure.

FIG. 6B is the photograph of detecting the signal of labeled oligonucleotide that bound to the target DNA after triple strand DNA structure was electrophoresed.

FIG. 6C is the photograph of staining gel with ethidium bromide after electrophoresis. Each lane is as follows:

Lane 1: The heat treatment was conducted at 25° C. for 10 minutes using oligonucleotide 1.

Lane 2: The reaction was performed in the same manner of lane 1 in which the heat treatment was conducted at 65° C. for 10 minutes.

Lane 3: The reaction was performed in the same manner of lane 1 in which the heat treatment was conducted at 70° C. for 10 minutes.

Lane 4: The reaction was performed in the same manner of lane 1 in which the heat treatment was conducted at 75° C. for 10 minutes.

Lane 5: The reaction was performed in the same manner of lane 1 in which the heat treatment was conducted at 80° C. for 10 minutes.

Lane 6: The reaction was performed in the same manner of lane 1 in which the heat treatment was conducted at 85° C. for 10 minutes.

Lane 7: The reaction was performed in the same manner of lane 1 in which the heat treatment was conducted at 90° C. for 10 minutes.

Lane 8: The reaction was performed in the same manner of lane 1 in which the heat treatment was conducted at 95° C. for 10 minutes.

Lane 9: The reaction was performed in the same manner of lane 1 in which oligonucleotide 16 was used.

Lane 10 The reaction was performed in the same manner of lane 2 in which oligonucleotide 16 was used.

Lane 11: The reaction was performed in the same manner of lane 3 in which oligonucleotide 16 was used.

Lane 12: The reaction was performed in the same manner of lane 4 in which oligonucleotide 16 was used.

Lane 13: The reaction was performed in the same manner of lane 5 in which oligonucleotide 16 was used.

Lane 14: The reaction was performed in the same manner of lane 6 in which oligonucleotide 16 was used.

Lane 15: The reaction was performed in the same manner of lane 7 in which oligonucleotide 16 was used.

Lane 16: The reaction was performed in the same manner of lane 8 in which oligonucleotide 16 was used.

Lane 17: After the reaction mixture including 1 pmol labeled oligonucleotide1, 10 pmol unlabeled oligonucleotide 2, 100 ng M13 mp18 ssDNA, 4.8 mM ATP-γS, 30 mM Tris acetate (pH 7.2), and 20 mM magnesium acetate was incubated at 37° C. for 30 minutes, 0.5% (W/Vol) SDS and 0.7 mg/ml proteinase K was added to the mixture. Then, the mixture was incubated at 37° C. for 30 minutes. Subsequent reaction was performed in the same manner of lane 1.

Lane 18: The reaction was performed in the same manner of lane 17 in which the reaction mixture was treated with heat at 65° C. for 10 minutes.

Lane 19: The reaction was performed in the same manner of lane 17 in which the reaction mixture was treated with heat at 70° C. for 10 minutes.

Lane 20: The reaction was performed in the same manner of lane 17 in which the reaction mixture was treated with heat at 75° C. for 10 minutes.

Lane 21: The reaction was performed in the same manner of lane 17 in which the reaction mixture was treated with heat at 80° C. for 10 minutes.

Lane 22: The reaction was performed in the same manner of lane 17 in which the reaction mixture was treated with heat at 85° C. for 10 minutes.

Lane 23: The reaction was performed in the same manner of lane 17 in which the reaction mixture was treated with heat at 90° C. for 10 minutes.

Figure 7:
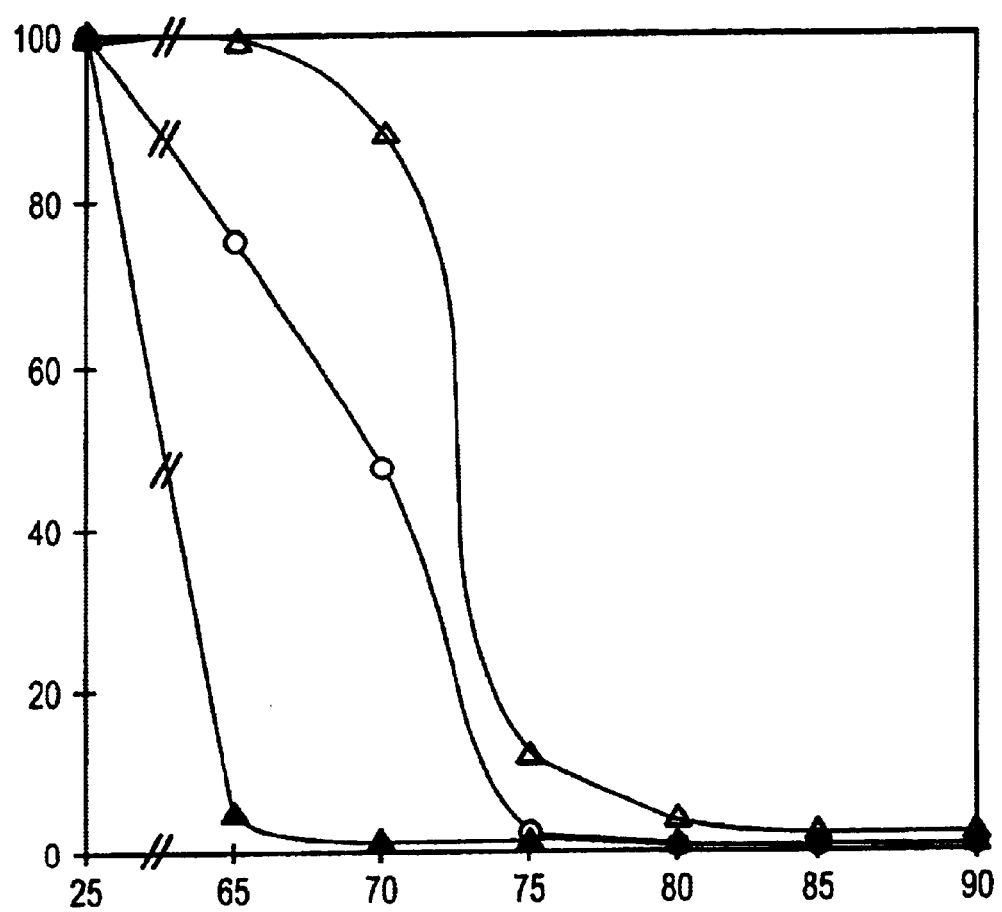

FIG. 7 shows the intensity of the signal from the labeled oligonucleotide, measured by BAS2000 Image analyzer, and the result. Longitudinal axis indicates the temperature (° C). Triangles show the result of lane 1 to 8 while black triangles show the result of lane 9 to 16. Circles show the result of lane 17 to 23.

Figure 8:
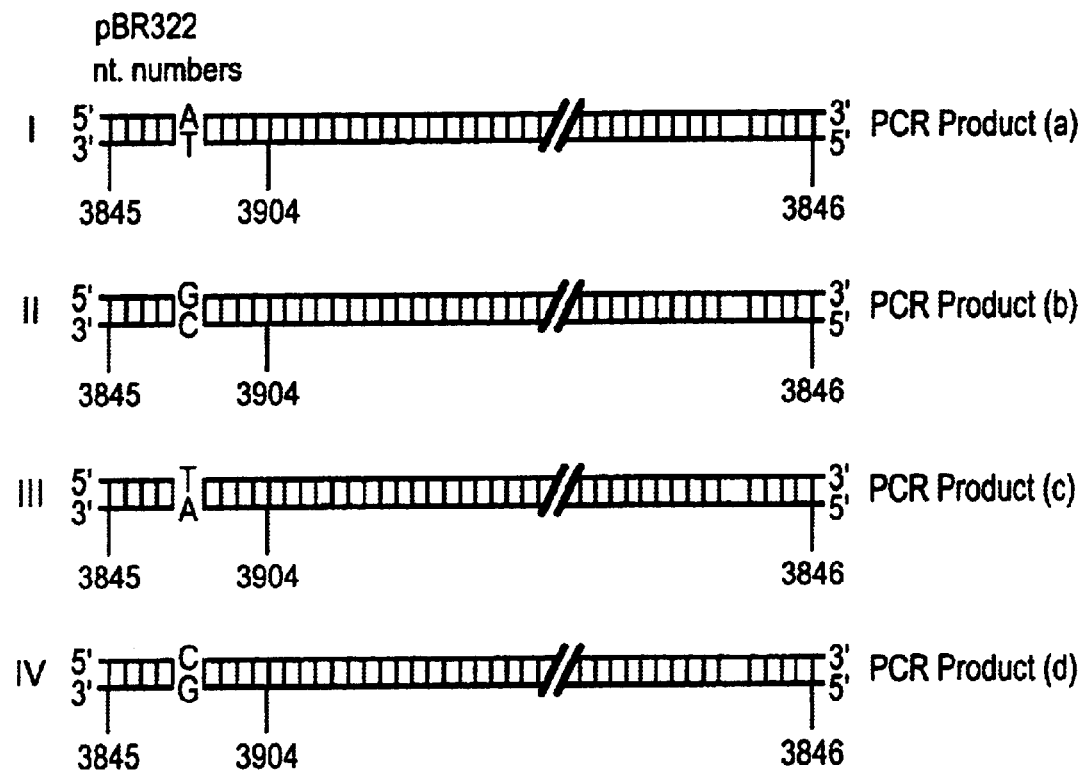

FIG. 8 schematically shows the relation of the position between target DNA (PCR product) used for the experiment and the oligonucleotide containing sequence complementary to the DNA. "A", "T", "G" or "C" on the oligonucleotide indicates the types of the nucleotide located at corresponding base pair of the target DNA shown just described above in character in the figure.

Figure 9A:
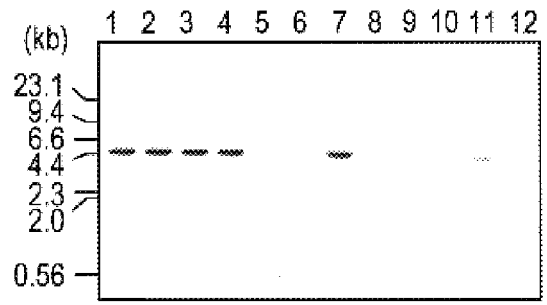
Figure 9A:
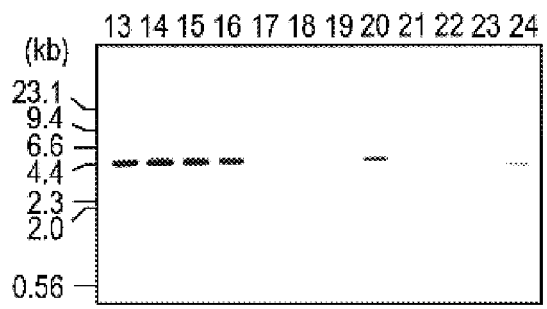
Figure 9A:
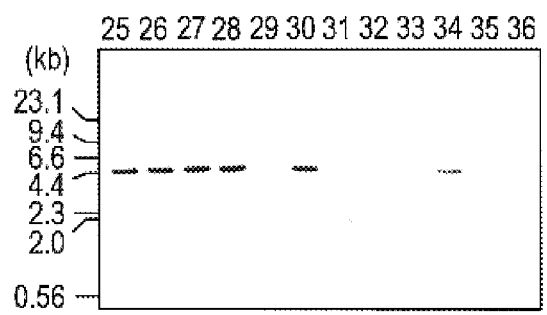
Figure 9A:
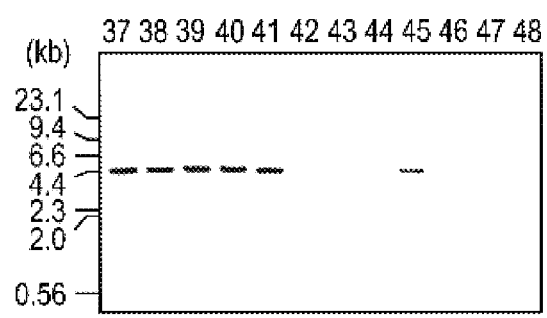
Figure 9B:
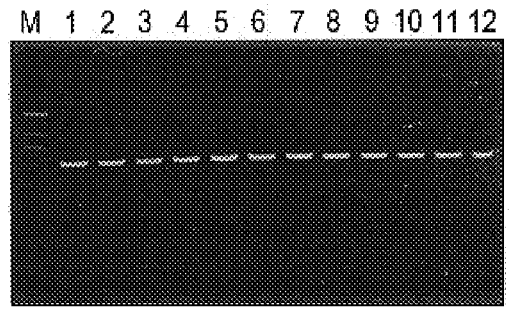
Figure 9B:
Figure 9B:
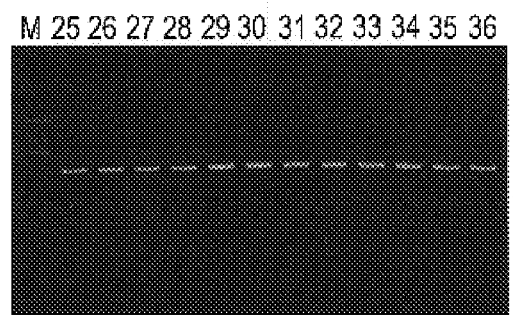
Figure 9B:
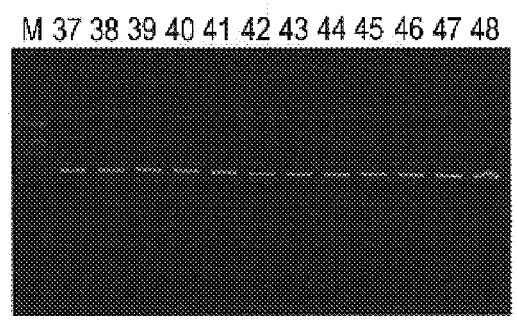

FIGS. 9A–9B show the following:

FIG. 9A is the photograph of detecting the signal of labeled oligonucleotide that bound to the target DNA after triple strand DNA structure was electrophoresed.

FIG. 9B is the photograph of staining gel corresponding to FIG. 9A with ethidium bromide after electrophoresis. Each lane is as follows:

Lane 1: The reaction was performed in the same manner of lane 1 of FIGS. 6B–6C in which PCR product was used as the target DNA, and oligonucleotide 3 was used.

Lane 2: The reaction was performed in the same manner of lane 1 in which oligonucleotide 17 was used.

Lane 3: The reaction was performed in the same manner of lane 1 in which oligonucleotide 18 was used.

Lane 4: The reaction was performed in the same manner of lane 1 in which oligonucleotide 19 was used.

Lane 5: The reaction was performed in the same manner of lane 1 in which the reaction mixture was treated with heat at 70° for 10 minutes after unused oligonucleotide was removed by S-400 spin column.

Lane 6: The reaction was performed in the same manner of lane 2 in which the reaction mixture was treated with heat at 70° C. for 10 minutes.

Lane 7: The reaction was performed in the same manner of lane 3 in which the reaction mixture was treated with heat at 70° C. for 10 minutes.

Lane 8: The reaction was performed in the same manner of lane 4 in which the reaction mixture was treated with heat at 70° C. for 10 minutes.

Lane 9: The reaction was performed in the same manner of lane 1 in which the reaction mixture was treated with heat at 80° C. for 10 minutes.

Lane 10: The reaction was performed in the same manner of lane 2 in which the reaction mixture was treated with heat at 80° C. for 10 minutes.

Lane 11: The reaction was performed in the same manner of lane 3 in which the reaction mixture was treated with heat at 80° C. for 10 minutes.

Lane 12: The reaction was performed in the same manner of lane 4 in which the reaction mixture was treated with heat at 80° C. for 10 minutes.

Lane 13: The reaction was performed in the same manner of lane in which the PCR Product (b) that was obtained by the PCR using primer 3 and primer 2 was used as the target DNA.

Lane 14: The reaction was performed in the same manner of lane 13 in which oligonucleotide 17 was used.

Lane 15: The reaction was performed in the same manner of lane 13 in which oligonucleotide 18 was used.

Lane 16: The reaction was performed in the same manner of lane 13 in which oligonucleotide 19 was used.

Lane 17: The reaction was performed in the same manner of lane 13 in which the reaction mixture was treated with heat at 70° C. for 10 minutes.

Lane 18: The reaction was performed in the same manner of lane 14 in which the reaction mixture was treated with heat at 70° C. for 10 minutes.

Lane 19: The reaction was performed in the same manner of lane 15 in which the reaction mixture was treated with heat at 70° C. for 10 minutes.

Lane 20: The reaction was performed in the same manner of lane 16 in which the reaction mixture was treated with heat at 70° C. for 10 minutes.

Lane 21: The reaction was performed in the same manner of lane 13 in which the reaction mixture was treated with heat at 80° C. for 10 minutes.

Lane 22: The reaction was performed in the same manner of lane 14 in which the reaction mixture was treated with heat at 80° C. for 10 minutes.

Lane 23: The reaction was performed in the same manner of lane 15 in which the reaction mixture was treated with heat at 80° C. for 10 minutes.

Lane 24: The reaction was performed in the same manner of lane 16 in which the reaction mixture was treated with heat at 80° C. for 10 minutes.

Lane 25: The reaction was performed in the same manner of lane 1 in which the PCR Product (c) that was obtained by the PCR using primer 4 and primer 2 was used as the target DNA.

Lane 26: The reaction was performed in the same manner of lane 25 in which oligonucleotide 17 was used.

Lane 27: The reaction was performed in the same manner of lane 25 in which oligonucleotide 18 was used.

Lane 28: The reaction was performed in the same manner of lane 25 in which oligonucleotide 19 was used.

Lane 29: The reaction was performed in the same manner of lane 25 in which the reaction mixture was treated with heat at 70° C. for 10 minutes.

Lane 30: The reaction was performed in the same manner of lane 26 in which the reaction mixture was treated with heat at 70° C. for 10 minutes.

Lane 31: The reaction was performed in the same manner of lane 27 in which the reaction mixture was treated with heat at 70° C. for 10 minutes.

Lane 32: The reaction was performed in the same manner of lane 28 in which the reaction mixture was treated with heat at 70° C. for 10 minutes.

Lane 33: The reaction was performed in the same manner of lane 25 in which the reaction mixture was treated with heat at 80° C. for 10 minutes.

Lane 34: The reaction was performed in the same manner of lane 26 in which the reaction mixture was treated with heat at 80° C. for 10 minutes.

Lane 35: The reaction was performed in the same manner of lane 27 in which the reaction mixture was treated with heat at 80° C. for 10 minutes.

Lane 36: The reaction was performed in the same manner of lane 28 in which the reaction mixture was treated with heat at 80° C. for 10 minutes.

Lane 37: The reaction was performed in the same manner of lane 1 in which the PCR Product (d) that was obtained by the PCR using primer 5 and primer 2 was used as the target DNA.

Lane 38: The reaction was performed in the same manner of lane 37 in which oligonucleotide 17 was used.

Lane 39: The reaction was performed in the same manner of lane 37 in which oligonucleotide 18 was used.

Lane 40: The reaction was performed in the same manner of lane 37 in which oligonucleotide 19 was used.

Lane 41: The reaction was performed in the same manner of lane 37 in which the reaction mixture was treated with heat at 70° C. for 10 minutes.

Lane 42: The reaction was performed in the same manner of lane 38 in which the reaction mixture was treated with heat at 70° C. for 10 minutes.

Lane 43: The reaction was performed in the same manner of lane 39 in which the reaction mixture was treated with heat at 70° C. for 10 minutes.

Lane 44: The reaction was performed in the same manner of lane 40 in which the reaction mixture was treated with heat at 70° C. for 10 minutes.

Lane 45: The reaction was performed in the same manner of lane 37 in which the reaction mixture was treated with heat at 80° C. for 10 minutes.

Lane 46: The reaction was performed in the same manner of lane 38 in which the reaction mixture was treated with heat at 80° C. for 10 minutes.

Lane 47: The reaction was performed in the same manner of lane 39 in which the reaction mixture was treated with heat at 80° C. for 10 minutes.

Lane 48: The reaction was performed in the same manner of lane 40 in which the reaction mixture was treated with heat at 80° C. for 10 minutes.

Figure 10A:
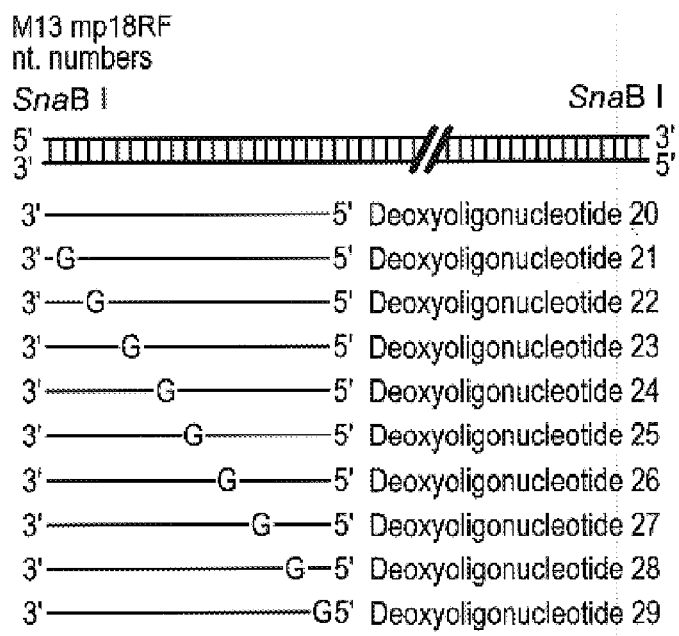
Figure 10B:
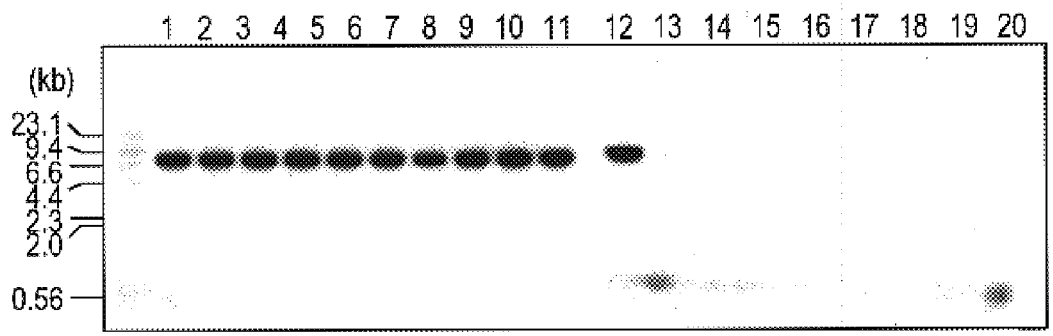
Figure 10C:
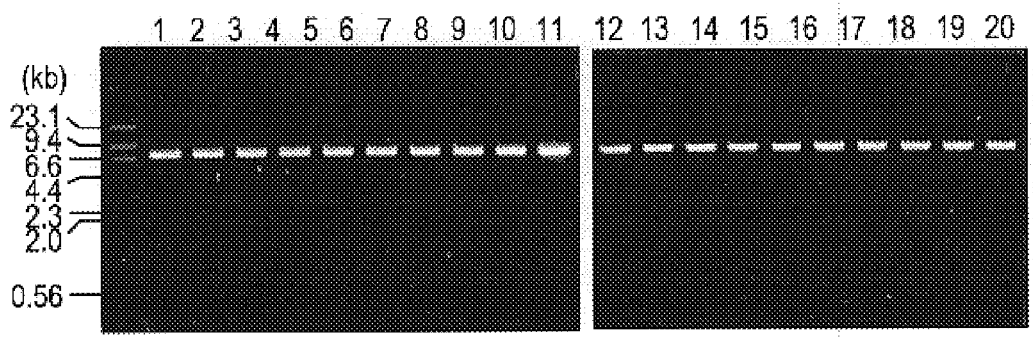

FIGS. 10A–10C show the following:

FIG. 10A schematically shows the relation of the position between target DNA used for the experiment and the oligonucleotide containing sequence complementary to the DNA. "G" on the oligonucleotide indicates the relative position of mutation.

FIG. 10B is the photograph of detecting the signal of labeled oligonucleotide that bound to the target DNA after triple strand DNA structure was electrophoresed.

FIG. 10C is the photograph of staining gel corresponding to FIG. 10B with ethidium bromide after electrophoresis. Each lane is as follows:

Lane 1: The reaction was performed in the same manner of lane 1 of FIGS. 6B–6C of Example 6 in which oligonucleotide 20 was used.

Lane 2: The reaction was performed in the same manner of lane 1 in which oligonucleotide 21 was used.

Lane 3: The reaction was performed in the same manner of lane 1 in which oligonucleotide 22 was used.

Lane 4: The reaction was performed in the same manner of lane 1 in which oligonucleotide 23 was used.

Lane 5: The reaction was performed in the same manner of lane 1 in which oligonucleotide 24 was used.

Lane 6: The reaction was performed in the same manner of lane 1 in which oligonucleotide 25 was used.

Lane 7: The reaction was performed in the same manner of lane 1 in which oligonucleotide 26 was used.

Lane 8: The reaction was performed in the same manner of lane 1 in which oligonucleotide 27 was used.

Lane 9: The reaction was performed in the same manner of lane 1 in which oligonucleotide 28 was used.

Lane 10: The reaction was performed in the same manner of lane 1 in which oligonucleotide 29 was used.

Lane 11: The reaction was performed in the same manner of lane 1 in which the reaction mixture was treated with heat at 80° C. for 10 minutes.

Lane 12: The reaction was performed in the same manner of lane 2 in which the reaction mixture was treated with heat at 80° C. for 10 minutes.

Lane 13: The reaction was performed in the same manner of lane 3 in which the reaction mixture was treated with heat at 80° C. for 10 minutes.

Lane 14: The reaction was performed in the same manner of lane 4 in which the reaction mixture was treated with heat at 80° C. for 10 minutes.

Lane 15: The reaction was performed in the same manner of lane 5 in which the reaction mixture was treated with heat at 80° C. for 10 minutes.

Lane 16: The reaction was performed in the same manner of lane 6 in which the reaction mixture was treated with heat at 80° C. for 10 minutes.

Lane 17: The reaction was performed in the same manner of lane 7 in which the reaction mixture was treated with heat at 80° C. for 10 minutes.

Lane 18: The reaction was performed in the same manner of lane 8 in which the reaction mixture was treated with heat at 80° C. for 10 minutes.

Lane 19: The reaction was performed in the same manner of lane 9 in which the reaction mixture was treated with heat at 80° C. for 10 minutes.

Lane 20: The reaction was performed in the same manner of lane 10 in which the reaction mixture was treated with heat at 80° C. for 10 minutes.

Figure 11:
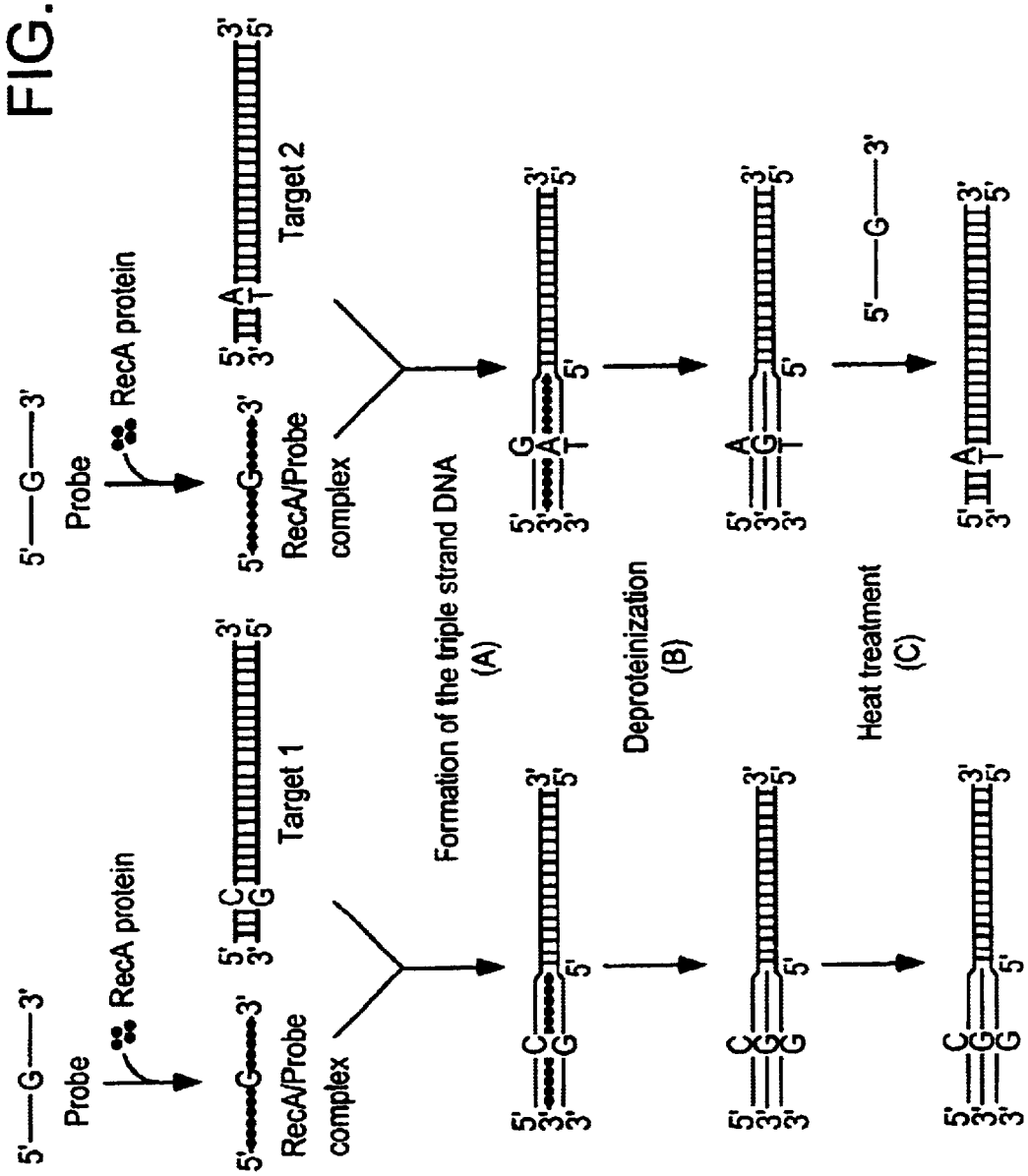

FIG. 11 schematically shows the method for detecting of this invention.

Figure 12A:
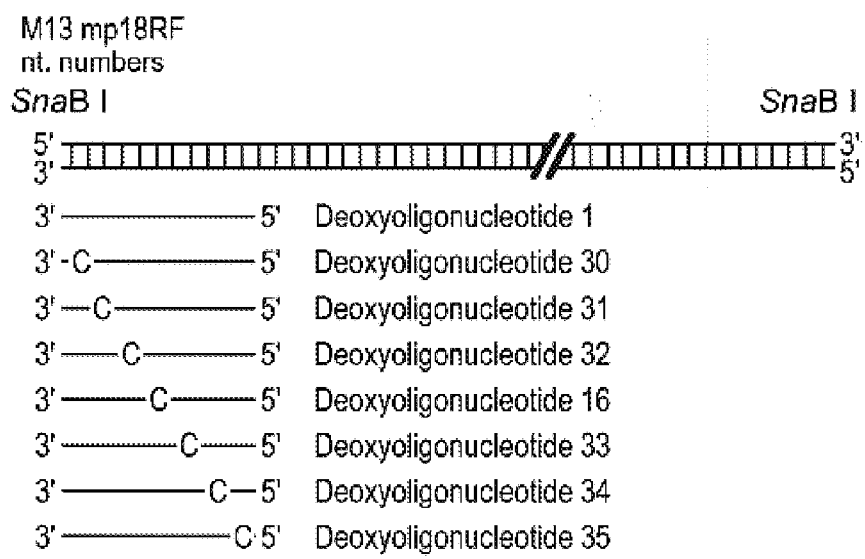
Figure 12B:
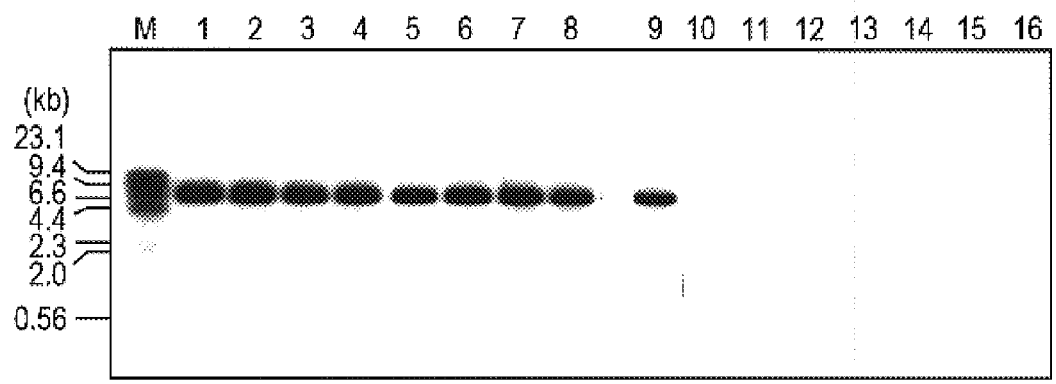
Figure 12C:
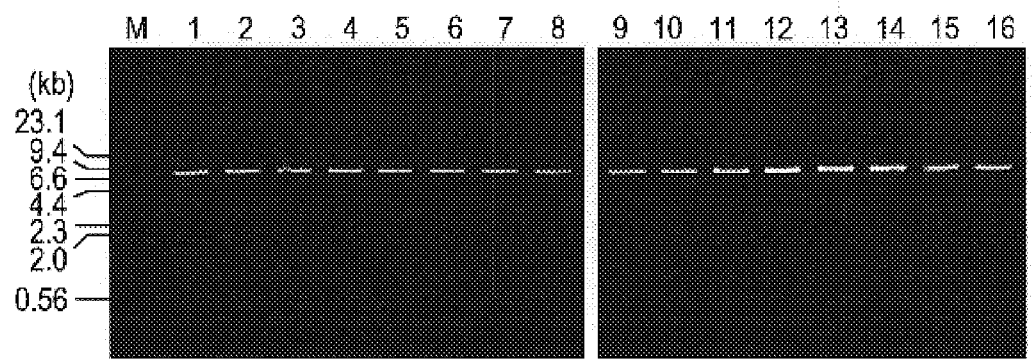

FIGS. 12A–12C show the following:

FIG. 12A schematically shows the relation of the position between target DNA used for the experiment and the oligonucleotide containing sequence complementary to the DNA. "C" on the oligonucleotide indicates the relative position of mutation.

FIG. 12B is the photograph of detecting the signal of labeled oligonucleotide that bound to the target DNA after triple strand DNA structure was electrophoresed.

FIG. 12C is the photograph of staining gel with ethidium bromide after electrophoresis. Each lane is as follows:

Lane 1: The reaction was performed in the same manner of lane 1 of FIGS. 6B–6C of Example 6.

Lane 2: The reaction was performed in the same manner of lane 1 in which oligonucleotide 30 was used.

Lane 3: The reaction was performed in the same manner of lane 1 in which oligonucleotide 31 was used.

Lane 4: The reaction was performed in the same manner of lane 1 in which oligonucleotide 32 was used.

Lane 5: The reaction was performed in the same manner of lane 1 in which oligonucleotide 16 was used.

Lane 6: The reaction was performed in the same manner of lane 1 in which oligonucleotide 33 was used.

Lane 7: The reaction was performed in the same manner of lane 1 in which oligonucleotide 34 was used.

Lane 8: The reaction was performed in the same manner of lane 1 in which oligonucleotide 35 was used.

Lane 9: The reaction was performed in the same manner of lane 1 in which the reaction mixture was treated with heat at 70° C. for 10 minutes.

Lane 10: The reaction was performed in the same manner of lane 2 in which the reaction mixture was treated with heat at 70° C. for 10 minutes.

Lane 11: The reaction was performed in the same manner of lane 3 in which the reaction mixture was treated with heat at 70° C. for 10 minutes.

Lane 12: The reaction was performed in the same manner of lane 4 in which the reaction mixture was treated with heat at 70° C. for 10 minutes.

Lane 13: The reaction was performed in the same manner of lane 5 in which the reaction mixture was treated with heat at 70° C. for 10 minutes.

Lane 14: The reaction was performed in the same manner of lane 6 in which the reaction mixture was treated with heat at 70° C. for 10 minutes.

Lane 15: The reaction was performed in the same manner of lane 7 in which the reaction mixture was treated with heat at 70° C. for 10 minutes.

Lane 16: The reaction was performed in the same manner of lane 8 in which the reaction mixture was treated with heat at 70° C. for 10 minutes.

Figure 13A:
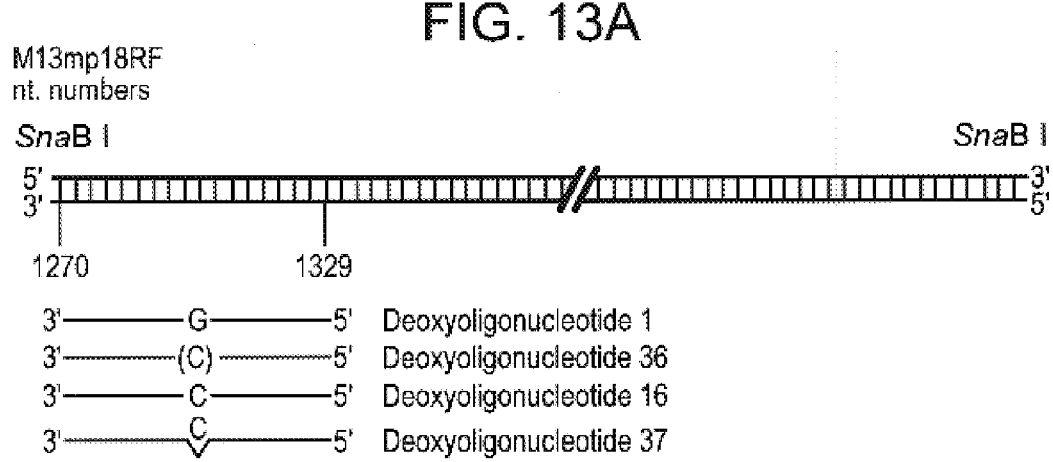
Figure 13B:
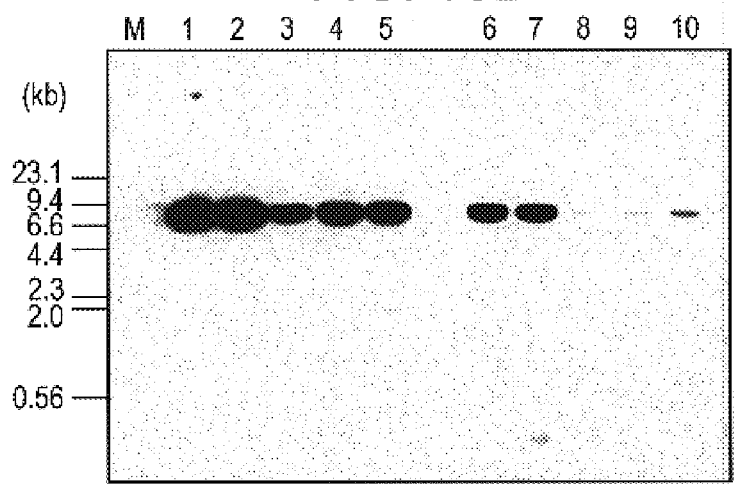

FIGS. 13A–13B show the following:

FIG. 13A schematically shows the relation of the position between target DNA used for the experiment and the oligonucleotide containing sequence complementary to the DNA.

FIG. 13B is the photograph of detecting the signal of labeled oligonucleotide that bound to the target DNA after triple strand DNA structure was electrophoresed.

Figure 13C:
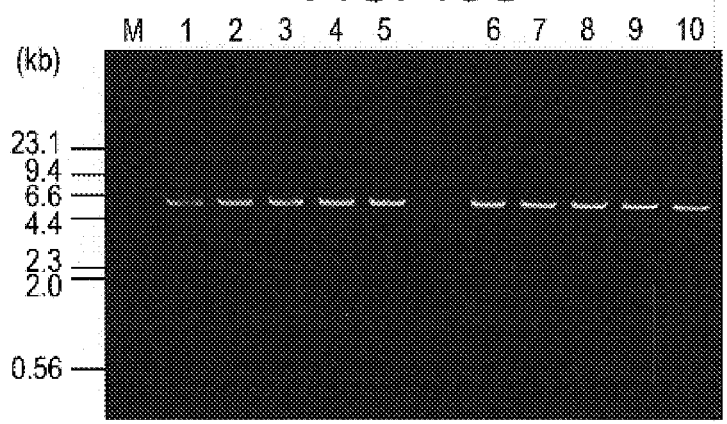

FIG. 13C is the photograph of staining gel with ethidium bromide after electrophoresis. Each lane is as follows:

Lane 1 and 2: The reaction was performed in the same manner of lane 1 of FIGS. 1B–1C of Example 1.

Lane 3: The reaction was performed in the same manner of lane 1 in which oligonucleotide 36 that had insertion mutation was used.

Lane 4: The reaction was performed in the same manner of lane 1 in which oligonucleotide 16 that had mismatch mutation was used.

Lane 5: The reaction was performed in the same manner of lane 1 in which oligonucleotide 37 that had deletion mutation was used.

Lane 6: The reaction was performed in the same manner of lane 1 in which the reaction mixture was treated with the heat at 70° C. for 10 minutes.

Lane 7: The reaction was performed in the same manner of lane 2 in which the reaction mixture was treated with the heat at 70° C. for 10 minutes.

Lane 8: The reaction was performed in the same manner of lane 3 in which the reaction mixture was treated with the heat at 70° C. for 10 minutes.

Lane 9: The reaction was performed in the same manner of lane 4 in which the reaction mixture was treated with the heat at 70° C. for 10 minutes.

Lane 10: The reaction was performed in the same manner of lane 5 in which the reaction mixture was treated with the heat at 70° C. for 10 minutes.

DETAILED DESCRIPTION OF THE INVENTION

The present invention provides a novel method for detecting polymorphism in target DNA using homologous recombination protein. In this method, double strand DNA containing test polymorphic site, an oligonucleotide probe that hybridizes to a region containing polymorphic site of the double strand DNA, and a homologous recombination protein are contacted under the condition in which triple strand DNA complex is formed (step (a); referred to FIG. 11(A)).

In this invention, "polymorphism" means the individual difference in genome of identical species. The polymorphism containing the difference of a nucleotide is preferred in this invention. Such "polymorphism" includes SNP (single nucleotide polymorphism) in which a nucleotide is substituted for another nucleotide. A mutation in which a nucleotide is inserted or deleted is also included.

"Detection of polymorphism" in this invention includes not only the determination of existence of polymorphism but also the discrimination of the type of nucleotides substituted (A: adenine, T: thymidine, G: guanine, or C: cytosine), which is called "genotyping" when the polymorphism is above-mentioned SNP.

"Test polymorphic site" in this invention indicates a nucleotide in DNA sequence where a polymorphism to be detected exists. "Double strand DNA containing test polymorphic site" indicates a double strand DNA whose DNA sequence contains test polymorphic site (it is also described simply as "target double strand DNA" or "target DNA" in this specification). As the target double strand DNA, genome DNA including "test polymorphic site" is raised specifically, but is not to be construed as being limited thereto. For example, DNA fragment obtained by amplifying a DNA region containing "test polymorphic site" can be used as a target double strand DNA in this invention. When "test polymorphic site" exists in open reading frame (ORF), double strand DNA fragment amplified by RT-PCR using RNA which is a transcriptional product as a template (cDNA) can be used as a target double strand DNA in this invention.

A target double strand DNA can be circular double strand DNA that has no DNA terminus and linear DNA that has DNA terminus. A DNA terminus of linear DNA is preferred to be blunt end, but can be an end having a structure in which one strand is over hanged.

"Test polymorphic site" in target double strand DNA is preferred to be located within 20 base pair and more preferably 10 base pair from DNA terminus to raise the efficiency of the detection.

The length of "double strand DNA containing test polymorphic site" is not specially limited, however, it is preferably 40 base pair or more and more preferably 60 base pair or more for the efficient formation of triple strand DNA with oligonucleotide probe. Although there is no upper limit for the length, normally not more than 100 kb and more preferably not more than 50 kb can be used because PCR product is preferably used as a target double strand DNA.

The present invention can detect polymorphism in target double strand DNA whose length is not more than 200 base pair, which is difficult for known method.

Target double strand DNA of this invention can be labeled by markers such as fluorescent dye depending on the method for detecting oligonucleotide probe.

"Oligonucleotide probe" in this invention is an oligonucleotide used for the detection of polymorphism that hybridizes to the region containing test polymorphic site in target double strand DNA. The oligonucleotide probe comprises triple strand DNA with double strand DNA containing test polymorphic site by the act of homologous recombination protein in this invention. Therefore, "hybridizing" of oligonucleotide probe indicates noncovalent bond (hydrogen bond) of oligonucleotide probe and target double strand DNA to form triple strand DNA. Although the oligonucleotide probe should have sequence complementary to a strand of target double strand DNA containing test polymorphic site, it does not need to have sequence completely complementary to the target DNA. That is, the sequence should be complementary to the target DNA so that it can form triple strand DNA with target double strand DNA in the DNA region containing test polymorphic site using homologous recombination protein. When the polymorphic position is revealed previously, only a nucleotide located on corresponding polymorphic position can be the nucleotide that is not complementary to the target DNA to use in the state described below. That is, the nucleotide at the polymorphic site in the oligonucleotide probe can be A (adenine), T (thymine), G (guanine), or C (cytosine) depending on the purpose.

Although the length of DNA sequence complementary to the DNA region containing test polymorphic site in oligonucleotide probe sequence is not specifically limited as far as it can form triple strand DNA with target double strand DNA, normally from 20 to 120 base, preferably from 40 to 120 base, and more preferably from 60 to 120 base can be used.

Although the whole length of oligonucleotide probe is not also specifically limited as far as it can form triple strand DNA with target double strand DNA, normally from 20 to 150 base, preferably from 120 base or less, and more preferably 60 base or less can be used.

Oligonucleotide probe of this invention is preferred to be labeled for the detection. Labeling of the oligonucleotide probe can be conducted by the general method by one skilled in the art. For example, the oligonucleotide probe can be labeled with radioisotope ($^{32}P$, $^{35}S$, $^{3}H$ etc.), fluorescent dye, and enzymatic marker producing detectable signal. The enzymatic marker is preferred to be stable to heat considering the step of heat treatment of this invention.

"Homologous recombination protein" of this invention can be any protein regardless of its origin as far as target double strand DNA and oligonucleotide probe can form stable triple strand DNA through the protein. Specifically, RecA protein derived from *Escherichia coli* and *Thermus thermophilus*, multifunctional protein encoded by recA gene derived from other enterobacteria, and proteins similar to RecA protein derived from *Agrobacterium tumefaciens, Bacillus subtilis, Methylophilus methylotrophus, Vibrio cholerae*, and *Ustilago maydis* can be used as a homologous recombination proteins. Proteins similar to RecA protein derived from *Saccharomyces cerevisiae* and human are also included in homologous recombination protein of this invention. Among these proteins, RecA protein derived from *Escherichia coli* and protein having similar function (for example, whole or a fragment of protein that is modified from the above-mentioned protein) is preferred in view of availability, stability, and functionality. As a modified protein, recA gene product produced by site-directed mutagenesis, which has one or several amino acids deleted, substituted or added and has ability to form triple strand DNA as RecA protein, can be used. A protein and a peptide containing single strand DNA binding domain of RecA protein are included in modified protein having several deleted amino acids. Example of this peptide can be that described in Voloshin et al., Science, Vol. 272, 1996: 868–872. "Protein" of this invention includes peptide.

Figure 5:
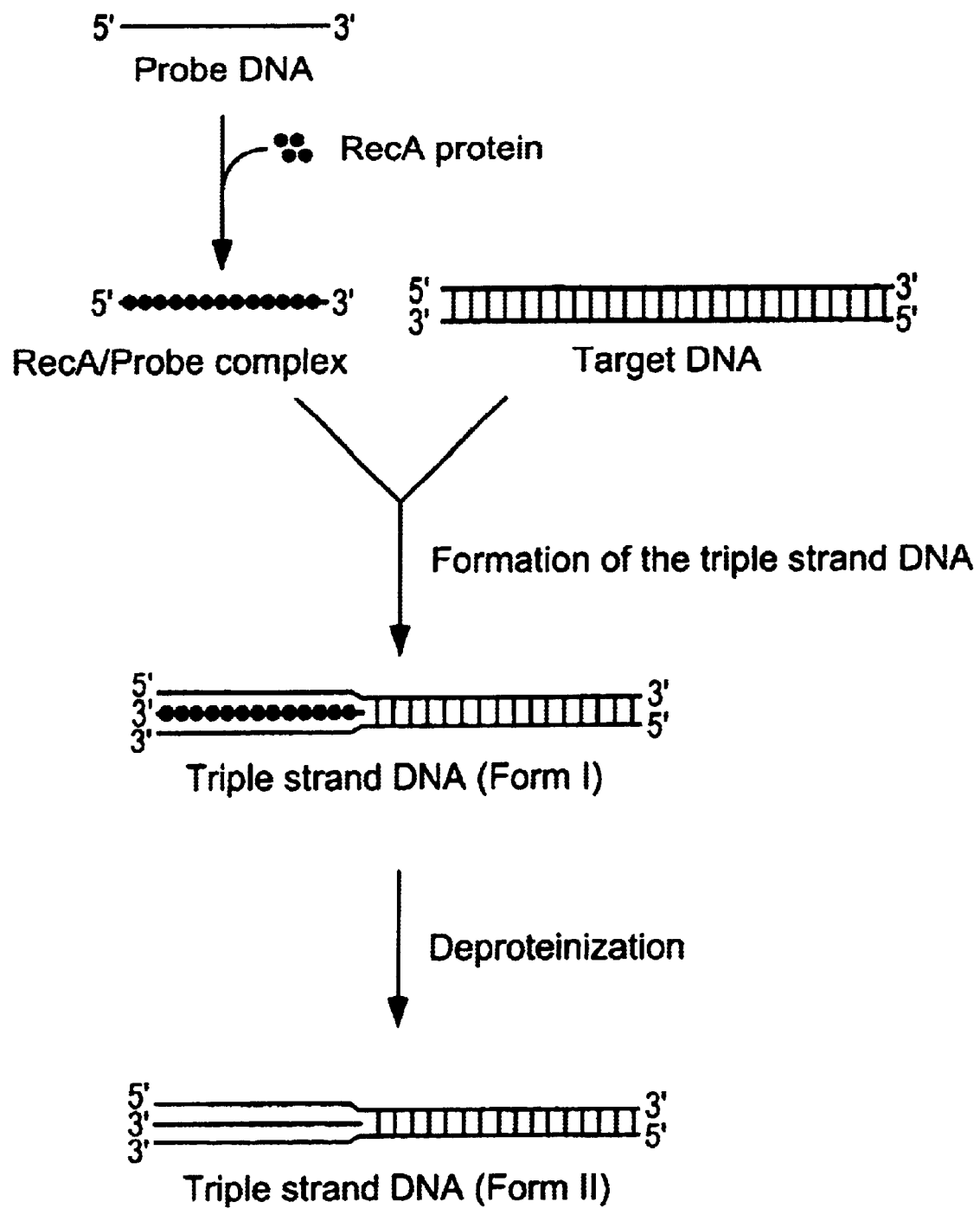

In this invention, above-mentioned target double strand DNA, oligonucleotide probe that hybridizes to the region containing polymorphic site of the target double strand DNA, and homologous recombination protein are contacted to form triple strand DNA. The formation of the triple strand DNA typically occurs as indicated in FIG. 5 schematically. In the step of the above-mentioned contact, coexistence of trinucleoside triphosphates (dATP, dUTP, dCTP, dTTP, dGTP, ATP, TTP, CTP, UTP, GTP) is preferred or necessary. As trinucleoside triphosphates, adenosine 5'-triphosphate (ATP), its derivatives such as adenosine$\gamma$-thio-triphosphate (ATP-$\gamma$S), GDP-$\gamma$S, and AMP-PNP, regeneration system of NTP (ATP, TTP, GTP, CTP) that includes NTP, phosphocreatine, and creatine phosphokinase can be used. When ATP, for example, is degraded biologically in the system of forming above-mentioned complex, ATP-$\gamma$S is preferably used.

The above-mentioned contact is performed in solution that is allowed to be buffered with suitable liquid such as buffer. When a buffering agent is used, for example, a Tris buffer derivative whose pH is adjusted to 6.5 to 7.5 and preferably about 7.2 with Tris (for example, tris (hydroxymethyl)aminomethane) and suitable acid (such as acetic acid, hydrochloric acid, etc.) is used. A buffering agent is generally used at the concentration of 10 mM–50 mM, preferably around 30 mM. In such solution, above-mentioned "contact" is conducted in which above-mentioned target double strand DNA, oligonucleotide probe, and homologous recombination protein are mixed and incubated with nucleoside triphosphate depending on the necessity.

Any proportion of target double strand DNA and oligonucleotide probe can be used as far as it does not have bad effect on the formation of triple strand DNA. The proportion of homologous recombination protein used varies depending on the length of target double strand DNA and oligonucleotide probe which comprise triple strand DNA structure. Generally, the molar amount of the protein is larger than that of each strand comprising triple strand DNA. 1 molar protein for three nucleotides is preferred.

The above-mentioned mixture prepared is incubated at 4–54° C., preferably about 37° C., for 15 minutes or more, generally for 30 minutes so that triple strand DNA is formed.

Above-mentioned triple strand DNA thus formed exists in the form of complex (herein, denoted as "triple strand DNA complex") in which homologous recombination protein normally binds to at least part of the triple strand DNA. "Triple strand DNA complex" in this invention means the structure in which homologous recombination protein binds to triple strand DNA. Triple strand DNA complex can be isolated from reaction mixture by the purification method such as phenol-chloroform extraction, gel filtration, and various electrophoresis. The complex thus isolated is stable under normal ex vivo physiological conditions.

The order of contacting double strand DNA containing test polymorphic site, oligonucleotide probe hybridizing the region that contains polymorphic site in the double strand DNA, and homologous recombination protein is not limited specifically in the step of (a). Preferably, after homologous recombination protein is contacted with oligonucleotide probe and forms homologous recombination protein/probe complex, double strand DNA containing test polymorphic site is contacted with the complex.

The homologous recombination protein is removed from the triple strand DNA formed in the step of (a) in this invention (step (b); referred to FIG. 11(B)).

In the step, the homologous recombination protein can be removed from the triple strand DNA complex by the treatment of the homologous recombination protein with protein degradation enzyme usually.

A protein degradation enzyme is generally called "protease", "proteinase", or "peptidase", which is included in the protein degradation enzyme of this invention. For example, proteinase K and such can be properly used as the protein degradation enzyme of this invention. One skilled in the art can judge suitable reaction mixture and condition to conduct protein degradation enzyme treatment corresponding to the types of used enzyme. Specifically, the reaction temperature is preferred to be 37° C. and the reaction time is preferred to be 20 minutes or more. Also the reaction temperature is preferred to be not more than 50° C.

Moreover, the homologous recombination protein can be removed from the triple strand DNA complex by SDS (sodium dodecyl sulfate) treatment, guanidine hydrochloride treatment, and heat treatment.

The triple strand DNA complex deproteinized is also stable under normal ex vivo physiological conditions.

After the step, oligonucleotide probe that does not form triple strand DNA can be removed.

Secondly in the present invention, the triple strand DNA is treated with heat under the condition in which oligonucleotide probes is released from triple strand DNA from which homologous recombination protein was removed if the test polymorphic site in the target double strand DNA is not complementary to the corresponding site in oligonucleotide probe (step (c); referred to FIG. 11(C)).

"The test polymorphic site in the target double strand DNA is not complementary to the corresponding site in the oligonucleotide probe" means that the nucleotide in the polymorphic site is not complementary to the counterpart nucleotide in the oligonucleotide probe when the double strand DNA containing test polymorphic site hybridizes to oligonucleotide probe. When the polymorphism is an insertion or a deletion, the counterpart nucleotide in the oligonucleotide probe does not exist. However, above-mentioned "not complementary" includes this case.

The present inventors revealed that there is the difference in stability to heat between the triple strand DNA in which the test polymorphic site in the target double strand DNA is complementary to the corresponding site in oligonucleotide probe and in which it is not complementary. When the test polymorphic site in the target double strand DNA is not complementary to the corresponding site in oligonucleotide probe, the oligonucleotide probe (described as "mismatch probe" hereafter) comprising the triple strand DNA can be released by the heat treatment under the suitable condition. The condition of temperature, in which oligonucleotide probe is not released from the triple strand DNA in which the test polymorphic site in the target double strand DNA is complementary to the corresponding site in oligonucleotide probe and is released from the triple strand DNA in which the site is not complementary to the corresponding site, varies depending on the length of target double strand DNA comprising the triple strand DNA, the length of the oligonucleotide probe, and their DNA nucleotide sequences, the extent of the complementation, and composition of reaction mixture (such as the concentration of Tris). Optimal condition (such as composition of reaction mixture and temperature of heat treatment) can be suitably selected according to experiment and experience by one skilled in the art. Specifically, the condition indicated in Example 5 (FIGS. 6A–6C) can be used. Generally, when the concentration of Tris in the reaction mixture is decreased, the mismatch probe becomes easy to be released from the triple strand DNA. When the concentration of Tris is increased, the mismatch probe becomes hard to be released. Therefore, the concentration of Tris is preferred to be low when using long oligonucleotide probe while the concentration of Tris is preferred to be high when using short oligonucleotide probe.

Next, the oligonucleotide probe that binds to target double strand DNA and comprises triple strand DNA is detected in this invention (step (d)).

Preferred embodiment is to detect labeled oligonucleotide probe comprising triple strand DNA based on the property of the labeled marker. For example, when oligonucleotide probe is labeled with $^{32}P$ triple strand DNA complex formed by homologous recombination protein is deproteinized and treated with heat. Then the reaction mixture is electrophoresed with gel. Autoradiogram of the gel is obtained, and signal from labeled oligonucleotide is recorded on X ray film so that the signals can be detected. By examining the existence of bands on X ray film in this way, oligonucleotide probe that binds to the target double strand DNA and comprises the triple strand DNA after the heat treatment can be detected.

Preferred embodiment of the present invention is the detection of SNP that exists in the individual human genome. At first, the double strand DNA (target double strand DNA) that consists of the DNA region in which the existence of SNP is to be examined is prepared. The DNA could be the DNA fragment produced by the PCR amplification of the target double strand DNA. Also genome DNA cut using restriction enzyme recognition site and untreated genome DNA can be used as a target double strand DNA. Next, oligonucleotide probe that contains the nucleotide sequence complementary to one strand of the target double strand DNA fragment is constructed. The public nucleotide sequence data, for example, various human genome database can be used. When no oligonucleotide probe is detected by the method described above of the present invention, it is judged that SNP exists in the DNA region complementary to the oligonucleotide probe in the target double strand DNA (a nucleotide mutation exists in the test polymorphic site). While the existence of oligonucleotide probe that binds to triple strand DNA is detected, it is judged that no SNP exists in the DNA region complementary to the oligonucleotide probe in the target double strand DNA.

When polymorphic site is revealed previously, the types of the mutated nucleotide located at the polymorphic site can be determined by the detection method of this invention. One embodiment is preparing double strand DNA fragment (target double strand DNA) that contains the polymorphic site. Then, oligonucleotide probe that consists of the sequence complementary to one strand of the double strand DNA region containing the polymorphic site of the target double strand DNA is prepared. At that time, 4 types of oligonucleotide probes are made in which the nucleotide corresponding to the test polymorphic site are A (adenine), T (thymine), G (guanine), and C (cytosine). By this method, oligonucleotide probe that binds to triple strand DNA can be detected, and the types of the nucleotide located at the polymorphic site in the target DNA can be determined by the types of the nucleotide corresponding to the test polymorphic site in oligonucleotide probe. For example, when oligonucleotide probe in which A exists in the position corresponding to the test polymorphic site by the above-mentioned method, the types of the nucleotide in the test polymorphic site is determined as T.

The present invention also provides a kit for detecting polymorphism in target double strand DNA using homologous recombination protein. The kit of this invention includes at least the following components:

(a) an oligonucleotide probe that hybridizes to a double strand DNA containing a test polymorphic site, and (b) a homologous recombination protein. Details of (a) and (b) were described above.

The above-mentioned kit of this invention can include nucleotide triphosphate, a buffer agent, and a reagent removing the homologous recombination protein. The reagent removing homologous recombination protein includes proteins such as protein degradation enzymes and such.

The present invention provides a method for detecting polymorphism in the target DNA sequence using a homologous recombination protein. In this method, a target DNA and oligonucleotide probe for the detection of polymorphism forms triple strand DNA structure with a homologous recombination protein. As this triple strand DNA can be formed by DNA which is at least 40 bp long, long DNA region is not necessary for the search of DNA polymorphism. As the binding of probe and target DNA through the formation of triple strand DNA with a homologous recombination protein has higher specificity than that seen in normal hybridization, this method can detect polymorphism more sensitively than conventional method for detecting DNA polymorphism using general hybridization.

This invention is expectedly applicable to the detection of disease genes derived from DNA polymorphism, determination of disease sensitivity, and development of pharmaceutical.

Any patents, patent applications, and publications cited herein are incorporated by reference.

The present invention is illustrated in detail below with references to examples, but is not to be construed as being limited thereto.

EXAMPLE 1

Dependency of Each Reaction Component in the Formation of Triple Strand DNA

The experiment was conducted to examine reaction components when triple strand DNA was formed. M13 mp18 RF DNA cut with restriction enzyme SnaB I to make it linear as target double strand DNA and 60 mer oligonucleotide 1 and 2 that have terminal sequence of the target DNA were prepared. pBR322 DNA cut with restriction enzyme Sca I to make it linear and 60 mer oligonucleotide 3 that has terminal sequence of the target DNA were prepared as target DNA. Oligonucleotide 1, 2, and 3 have the direction of sequence indicated as upper part of FIG. 1A. 5'-terminal of oligonucleotide 1 was labeled with $^{32}$P using T4 polynucleotide kinase and [γ-$^{32}$P] ATP. Deproteinization was conducted by incubating 1 pmol labeled oligonucleotide 1, 3.0 μg RecA protein, 4.8 mM ATP-γS, and 200 ng target DNA with 20 mM magnesium acetate and 30 mM Tris acetate (pH 7.2) at 37° C. for 30 minutes, adding 0.5% (W/Vol) SDS and 0.7 mg/ml proteinase K, and then incubating) at 37° C. for 30 minutes. A half of the reaction mixture was electrophoresed with 1% agarose gel. The gel was stained with ethidium bromide, and the photograph of DNA was recorded. Gel was set on filter paper and was dried up in gel dryer. Autoradiogram of the gel was obtained, and signal from labeled oligonucleotide was recorded on X ray film. The result is shown in lane 1 of FIG. 1B. The nucleotide sequence of the oligonucleotides used were as follows:

```
Oligonucleotide 1:
5'-agaggctttg aggactaaag acttttcat gaggaagttt ccattaaacg ggtaaaatac-3'/  SEQ ID NO:1

Oligonucleotide 2:
5'-gtattttacc cgtttaatgg aaacttcctc atgaaaaagt ctttagtcct caaagcctct-3'/  SEQ ID NO:2

Oligonucleotide 3:
5'-acgccgggca agagcaactc ggtcgccgca tacactattc tcagaatgac ttggttgagt-3'/  SEQ ID NO:3
```

Figure 1C:
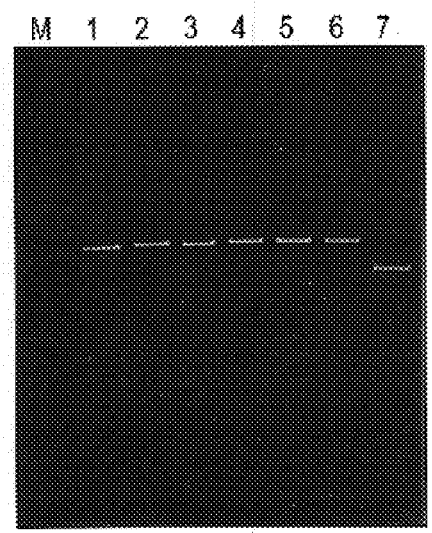

FIG. 1C shows the result of recording the photograph of the DNA after staining the electrophoresed gel with ethidium bromide.

Above-mentioned result revealed that RecA and ATP-γS were needed to be added in reaction for the formation of triple strand DNA as reaction components.

EXAMPLE 2

Orientation of Oligonucleotide Sequence Necessary for the Formation of Triple Strand DNA We examined the orientation of oligonucleotide sequence necessary for the formation of triple strand DNA. M13 mp18 RF DNA cut with restriction enzyme SnaB I to make it linear as target DNA and 60 mer oligonucleotide 1, 2, 4, and 5 that have both terminal sequence of the target DNA were prepared. The oligonucleotide has the orientation of sequence indicated as upper part of FIG. 2A. The condition of reaction was same as Example 1. The result is shown in FIG. 2B. The nucleotide sequence of the oligonucleotides used were as follows:

Oligonucleotide 4:
5'-tgttttagtg tattctttcg cctctttcgt tttaggttgg tgccttcgta gtggcattac-3'/ SEQ ID NO:4

Oligonucleotide 5:
5'-gtaatgccac tacgaaggca ccaacctaaa acgaaagagg cgaaagaata cactaaaaca-3'/ SEQ ID NO:5

FIG. 2C shows the result of recording the photograph of the DNA after staining the electrophoresed gel with ethidium bromide.

Above-mentioned result revealed that both terminal of the linear target DNA can form triple strand DNA and that the orientation of oligonucleotide sequence used must have the orientation of either sequence of both terminal sequences of target DNA.

EXAMPLE 3
Relation of the Position of Oligonucleotide Sequence Necessary for the Formation of Triple Strand DNA We examined the relation of the position of oligonucleotide sequence necessary for the formation of triple strand DNA. M13 mp18 RF DNA cut with restriction enzyme SnaB I to make it linear as target DNA, 60 mer oligonucleotide 1 that has terminal sequence of the target DNA, and oligonucleotide that has terminal sequence retaining from 10 to 40 base pair of the target DNA terminal were prepared. The condition of reaction was same as Example 1. The result is shown in FIG. 3(A). The nucleotide sequence of the oligonucleotides used were as follows:

is preffered to have target DNA sequence that starts inside sequence within 20 base from the terminal of the target DNA.

EXAMPLE 4

The Length of Oligonucleotide Sequence Necessary for the Formation of the Triple Strand DNA The experiment to examine the length of oligonucleotide sequence necessary for the formation of the triple strand DNA was carried out. M13 mp18 RF DNA cut with restriction enzyme SnaB I to make it linear as a target DNA and 20–80 MER oligonucleotide that has terminal sequence of the target DNA were prepared. The condition of reaction was same as Example 1. The result is shown in FIG. 4B. The nucleotide sequence of the oligonucleotides used were as follows:

Oligonucleotide 6:
5'-tccgatgctg tctttcgctg ctgagggtga cgatcccgca aaagcggcct ttaactccct-3'/ SEQ ID NO:6

Oligonucleotide 7:
5'-ctaccctcgt tccgatgctg tctttcgctg ctgagggtga cgatcccgca aaagcggcct-3'/ SEQ ID NO:7

Oligonucleotide 8:
5'-gtagccgttg ctaccctcgt tccgatgctg tctttcgctg ctgagggtga cgatcccgca-3'/ SEQ ID NO:8

FIG. 3C shows the result of recording the photograph of the DNA after staining the electrophoresed gel with ethidium bromide.

Above-mentioned result revealed that oligonucleotide sequence necessary for the formation of triple strand DNA Oligonucleotide 9:
5'-caaagcctct gtagccgttg ctaccctcgt tccgatgctg tctttcgctg ctgagggtga-3'/ SEQ ID NO:9

Oligonucleotide 10:
5'-ctttagtcct caaagcctct gtagccgttg ctaccctcgt tccgatgctg tctttcgctg -3'/ SEQ ID NO:10

Oligonucleotide 11:
5'-ctaccctcgt tccgatgctg tctttcgctg ctgagggtga cgatcccgca aaagcggcct ttaactccct gcaagcctca-3'/ SEQ ID NO:11

Oligonucleotide 12:
5'-ctgagggtga cgatcccgca aaagcggcct ttaactccct gcaagcctc-3'/ SEQ ID NO:12

Oligonucleotide 13:
5'-cgatcccgca aaagcggcct ttaactccct gcaagcctca-3'/ SEQ ID NO:13

FIG. 4C shows the result of recording the photograph of the DNA after staining the electrophoresed gel with ethidium bromide.

Above-mentioned result revealed that the length of oligonucleotide sequence necessary for the formation of the triple strand DNA is preferably 40 mer or more.

EXAMPLE 5
Thermostability of Triple Strand DNA

We examined the thermostability of triple strand DNA. M13 mp18 RF DNA cut with restriction enzyme SnaB I to make it linear as a target DNA and 60 mer oligonucleotide 1 that has terminal sequence of the target DNA were prepared. 5'-terminal of oligonucleotide 1 was labeled with $^{32}$P. The reaction mixture contains 1 pmol labeled oligonucleotide 1,200 ng target DNA, 3.0 μg RecA protein, 4.8 mM ATP-γS, 30 mM Tris acetate (pH 7.2), and 20 mM magnesium. After the reaction mixture was incubated at 37° C. for 30 minutes, 0.5% (W/Vol) SDS and 0.7 mg/ml proteinase K was added to the mixture. Then, the mixture was incubated at 37° C. for 30 minutes. After phenol-chloroform extraction was performed once, unused oligonucleotide was removed by twice manipulation of S-400 spin column (Amershain Pharmacia Biotech). After the whole reaction mixture was treated with heat at 25° C. for 10 minutes, half of that was electrophoresed with 1% agarose gel. After eletrophoresis, the gel was stained with ethidium bromide, and the photograph of DNA was recorded. Gel was set on filter paper and was dried up in gel dryer. Autoradiograin of the gel was obtained, and signal from labeled oligonucleotide was recorded on X ray film. The result is shown in lane 1 of FIG. 6B.

FIG. 6C shows the result of recording the photograph of the DNA after staining the electrophoresed gel with ethidium bromide. Intensity of the signals from labeled oligonucleotide from lane 1 to lane 23 were measured with BAS2000 Image analyzer and the result is shown in FIG. 7.

The result revealed that the thermostability of triple strand DNA using 60 mer oligonucleotide was around 70° C. although the thermostability of triple strand DNA containing mismatch was around 65° C.

EXAMPLE 6
Effect of the Types of Single Nucleotide Mutation

We examine the effect of the type of a nucleotide mutation in the oligonucleotide on the formation of triple strand DNA. The same reaction was conducted as lane 1 of FIG. 6B in Example 5 except using oligonucleotide 3 and PCR Product (a) as a target DNA. The result is shown in lane 1 of FIG. 9B. PCR reaction to prepare PCR Product (a) was conducted using 35-mer primer 1 that has the sequence same as the terminal sequence produced by cutting pBR322 DNA with reaction enzyme Sca I and 35-mer primer 2 that has the sequence of another terminal of the DNA as primers and 1 ng pBR322 DNA as template with 27 cycles of 98° C. for 20 seconds and 68° C. for 5 minutes following the general method. The part of the PCR product was electrophoresed with 1% agarose gel. The PCR Product (a) was extracted using QIAGEN Gel Extraction Kit and purified following the general method.

FIG. 9C shows the result of recording the photograph of the DNA after staining the electrophoresed gel with ethidium bromide. The nucleotide sequence of the oligonucleotides used were as follows:

```
Oligonucleotide 14:  5'-aaagcggcct ttaactccct gcaagcctca-3'/        SEQ ID NO:14

Oligonucleotide 15:  5'-ttaactccct gcaagcctca-3'/                   SEQ ID NO:15

Oligonucleotide 16:  5'-agaggctttg aggactaaag acttttttcat
                     Caggaagttt ccattaaacg ggtaaaatac-3'/           SEQ ID NO:16

Oligonucleotide 17:  5'-acgccgggca agagcaactc ggtcgccgca
                     Gacactattc tcagaatgac ttggttgagt-3'/           SEQ ID NO:17

Oligonucleotide 18:  5'-acgccgggca agagcaactc ggtcgccgca
                     Aacactattc tcagaatgac ttggttgagt-3'/           SEQ ID NO:18

Oligonucleotide 19:  5'-acgccgggca agagcaactc ggtcgccgca
                     Cacactattc tcagaatgac ttggttgagt-3'/           SEQ ID NO:19

Oligonucleotide 20:  5'-tgcgggatcg tcaccctcag cagcgaaaga
                     cagcatcgga acgagggtag caacggctac agaggctttg aggactaaag
                     acttttttcat gaggaagttt ccattaaacg ggtaaaatac-3'/ SEQ ID NO:20

Oligonucleotide 21:  5'-Ggcgggatcg tcaccctcag cagcgaaaga
                     cagcatcgga acgagggtag caacggctac agaggctttg aggactaaag
                     acttttttcat gaggaagttt ccattaaacg ggtaaaatac-3'/ SEQ ID NO:21

Oligonucleotide 22:  5'-tgcgggatcg tcacGctcag cagcgaaaga
                     cagcatcgga acgagggtag caacggctac agaggctttg aggactaaag
                     acttttttcat gaggaagttt ccattaaacg ggtaaaatac-3'/ SEQ ID NO:22
```

EXAMPLE 7
Effect of the Position of a Nucleotide Mutation in Oligonucleotide on the Sensitivity of Detection The effect of the position of a nucleotide mutation in oligonucleotide to the target DNA on the sensitivity of detection of SNP was examined. M13 mp18 RF DNA cut with restriction enzyme SnaB I to make it linear as a target DNA and oligonucleotide that has terminal sequence of the target DNA and has a substituted nucleotide were prepared. Then, the effect of the position of a nucleotide mutation in oligonucleotide on the sensitivity of detection was examined. The result is shown in FIGS. 10A–10C.

```
Oligonucleotide 23:  5'-tgcgggatcg tcaccctcag cagcgGaaga                       SEQ ID NO:23
                     cagcatcgga acgagggtag caacggctac agaggctttg aggactaaag
                     actttttcat gaggaagttt ccattaaacg ggtaaaatac-3'/

Oligonucleotide 24:  5'-tgcgggatcg tcaccctcag cagcgaaaga                       SEQ ID NO:24
                     cagcGtcgga acgagggtag caacggctac agaggctttg aggactaaag
                     actttttcat gaggaagttt ccattaaacg ggtaaaatac-3'/

Oligonucleotide 25:  5'-tgcgggatcg tcaccctcag cagcgaaaga                       SEQ ID NO:25
                     cagcatcgga acgagggtag Gaacggctac agaggctttg aggactaaag
                     actttttcat gaggaagttt ccattaaacg ggtaaaatac-3'/

Oligonucleotide 26:  5'-tgcgggatcg tcaccctcag cagcgaaaga                       SEQ ID NO:26
                     cagcatcgga acgagggtag caacggtac agaggctGtg aggactaaag
                     actttttcat
                     gaggaagttt ccattaaacg ggtaaaatac-3'/

Oligonucleotide 27:  5'-tgcgggatcg tcaccctcag cagcgaaaga                       SEQ ID NO:27
                     cagcatcgga acgagggtag caacggctac agaggctttg aggactaaag
                     actttGtcat gaggaagttt ccattaaacg ggtaaaatac-3'/

Oligonucleotide 28:  5'-tgcgggatcg tcaccctcag cagcgaaaga                       SEQ ID NO:28
                     cagcatcgga acgagggtag caacggctac agaggctttg aggactaaag
                     actttttcat gaggaGgttt ccattaaacg ggtaaaatac-3'/

Oligonucleotide 29:  5'-tgcgggatcg tcaccctcag cagcgaaaga                       SEQ ID NO:29
                     cagcatcgga acgagggtag caacggctac agaggctttg aggactaaag
                     actttttcat gaggaagttt ccattGaacg ggtaaaatac-3'/
```

As a result, it is revealed that the detection of SNP is possible when the position where the mutation was introduced is at the end.

Moreover, same experiment was performed using following oligonucleotides.

```
Oligonucleotide 1:
5'-agaggctttg aggactaaag actttttcat gaggaagttt ccattaaacg ggtaaaatac-3'/ SEQ ID NO:1

Oligonucleotide 30:
5'-Cgaggctttg aggactaaag actttttcat gaggaagttt ccattaaacg ggtaaaatac-3'/ SEQ ID NO:30

Oligonucleotide 31:
5'-agaggctttg Cggactaaag actttttcat gaggaagttt ccattaaacg ggtaaaatac-3'/ SEQ ID NO:31

Oligonucleotide 32:
5'-agaggctttg aggactaaag Cctttttcat gaggaagttt ccattaaacg ggtaaaatac-3'/ SEQ ID NO:32

Oligonucleotide 16:
5'-agaggctttg aggactaaag actttttcat Caggaagttt ccattaaacg ggtaaaatac-3'/ SEQ ID NO:16

Oligonucleotide 33:
5'-agaggctttg aggactaaag actttttcat gaggaagttC ccattaaacg ggtaaaatac-3'/ SEQ ID NO:33

Oligonucleotide 34:
5'-agaggctttg aggactaaag actttttcat gaggaagttt ccattaaacC ggtaaaatac-3'/ SEQ ID NO:34

Oligonucleotide 35:
5'-agaggctttg aggactaaag actttttcat gaggaagttt ccattaaacg ggtaaaatCc-3'/ SEQ ID NO:35
```

The result is shown in FIGS. 12A–12C. It is revealed that the detection of SNP is possible regardless of the types and the position of the mutation.

EXAMPLE 8
Detection of Deletion and Insertion of Nucleotide

M13 mp18 RF DNA cut with restriction enzyme SnaB I to make it linear as a target DNA and 60 mer oligonucleotide 1 that has terminal sequence of the target DNA were prepared. 5'-terminal of the oligonucleotide was labeled with $^{32}$P. The reaction mixture contains 1 pmol labeled oligonucleotide 1,200 ng target DNA, 3.0 μg RecA protein, 4.8 mM ATP-γS, 30 mM Tris acetate (pH 7.2), and 20 mM magnesium acetate. After the reaction mixture was incubated at 37° C. for 30 minutes, 0.5% (W/Vol) SDS and 0.7 mg/ml proteinase K was added to the mixture. Then, the mixture was incubated at 37° C. for 30 minutes. After phenol-chloroform extraction was performed once, unused oligonucleotide was removed by twice manipulation of S-400 spin column (Amersham Pharmacia Biotech). After the whole reaction mixture was treated with heat at 25° C. for 10 minutes, half of that was electrophoresed with 1% agarose gel. After electrophoresis, the gel was stained with ethidium bromide, and the photograph of DNA was recorded. Gel was set on filter paper and was dried up in gel dryer. Autoradiogram of the gel was obtained to detect signal which was recorded on X ray film. The result is shown in lane 1 of FIG. 13B.

The nucleotide sequence of the oligonucleotides used were as follows:

Oligonucleotide 36:
5'-agaggctttg aggactaaag acttttttcat gCaggaagttt ccattaaacg ggtaaaatac-3'/   SEQ ID NO:36

Oligonucleotide 37:
5'-agaggctttg aggactaaag acttttttcat aggaagttt ccattaaacg ggtaaaatac-3'/   SEQ ID NO:37

As a result, it is revealed that the detection of SNP is possible if the mutation is insertion or deletion.

What is claimed is:

1. A method for detecting a DNA polymorphism in a double strand DNA, said method comprising the steps of (a) to (e) below:
   (a) contacting (i) a double strand DNA comprising a test polymorphic site, (ii) an oligonucleotide probe that hybridizes to a region comprising said polymorphic site in said double strand DNA, and (iii) a homologous recombination protein under reaction conditions where a triple strand DNA complex is formed,
   (b) removing the homologous recombination protein from the triple strand DNA complex formed in the step (a), thereby generating a triple strand DNA,
   (c) conducting heat treatment of the triple strand DNA generated by removing the homologous recombination protein, under conditions where the oligonucleotide probe is released from said triple strand DNA, when the test polymorphic site in the double strand DNA is not complementary to a corresponding site in said oligonucleotide probe,
   (d) determining the existence or the absence of an oligonucleotide probe that binds to the double strand DNA to form the triple strand DNA,
   (e) judging that (i) SNP exists in the DNA region complementary to the oligonucleotide probe in the target double strand DNA when no oligonucleotide probe is detected, (ii) no SNP exists in the DNA region complementary to the oligonucleotide probe in the target double strand DNA when the existence of oligonucleotide probe that binds to triple strand DNA is detected.

2. The method of claim 1, wherein the double strand DNA comprising a test polymorphic site has a DNA terminus.

3. The method of claim 2, wherein the test polymorphic site is located within 20 bases from the DNA terminus.

4. The method of claim 1, wherein the length of the oligonucleotide probe is from 20 to 120 bases.

5. The method of claim 1, wherein the homologous recombination protein is a RecA protein from *E. coli*.

6. The method claim 1, wherein, in the step (a), a nucleotide triphosphate is added to the reaction system.

7. The method of claim 1, wherein, in the step (b), the homologous recombination protein is removed by conducting protein degradation enzyme treatment.

8. The method of claim 7, wherein the protein degradation enzyme is proteinase K.

* * * * *

SEQUENCE LISTING

<160> NUMBER OF SEQ ID NOS: 37

<210> SEQ ID NO 1
<211> LENGTH: 60
<212> TYPE: DNA
<213> ORGANISM: Artificial Sequence
<220> FEATURE:
<223> OTHER INFORMATION: Description of Artificial Sequence:Artificially
      Synthesized Oligonucleotide Sequence

<400> SEQUENCE: 1
agaggctttg aggactaaag accttttcat gaggaagttt ccattaaacg ggtaaaatac        60

<210> SEQ ID NO 2
<211> LENGTH: 60
<212> TYPE: DNA
<213> ORGANISM: Artificial Sequence
<220> FEATURE:
<223> OTHER INFORMATION: Description of Artificial Sequence:Artificially
      Synthesized Oligonucleotide Sequence

<400> SEQUENCE: 2 gtatttacc cgtttaatgg aaacttcctc atgaaaaagt ctttagtcct caaagcctct        60

<210> SEQ ID NO 3
<211> LENGTH: 60
<212> TYPE: DNA
<213> ORGANISM: Artificial Sequence
<220> FEATURE:
<223> OTHER INFORMATION: Description of Artificial Sequence:Artificially
      Synthesized Oligonucleotide Sequence

<400> SEQUENCE: 3
acgccgggca agagcaactc ggtcgccgca tacactattc tcagaatgac ttggttgagt        60

<210> SEQ ID NO 4
<211> LENGTH: 60
<212> TYPE: DNA
<213> ORGANISM: Artificial Sequence
<220> FEATURE:
<223> OTHER INFORMATION: Description of Artificial Sequence:Artificially
      Synthesized Oligonucleotide Sequence

<400> SEQUENCE: 4
tgttttagtg tattctttcg cctctttcgt tttaggttgg tgccttcgta gtggcattac        60

<210> SEQ ID NO 5
<211> LENGTH: 60
<212> TYPE: DNA
<213> ORGANISM: Artificial Sequence
<220> FEATURE:
<223> OTHER INFORMATION: Description of Artificial Sequence:Artificially
      Synthesized Oligonucleotide Sequence

<400> SEQUENCE: 5
gtaatgccac tacgaaggca ccaacctaaa acgaaagagg cgaaagaata cactaaaaca        60

<210> SEQ ID NO 6
<211> LENGTH: 60
<212> TYPE: DNA
<213> ORGANISM: Artificial Sequence
<220> FEATURE:
<223> OTHER INFORMATION: Description of Artificial Sequence:Artificially
      Synthesized Oligonucleotide Sequence

<400> SEQUENCE: 6
tccgatgctg tctttcgctg ctgagggtga cgatcccgca aaagcggcct ttaactccct        60

<210> SEQ ID NO 7
<211> LENGTH: 60
<212> TYPE: DNA
<213> ORGANISM: Artificial Sequence
<220> FEATURE:
<223> OTHER INFORMATION: Description of Artificial Sequence:Artificially
      Synthesized Oligonucleotide Sequence

<400> SEQUENCE: 7
ctaccctcgt tccgatgctg tctttcgctg ctgagggtga cgatcccgca aaagcggcct        60

<210> SEQ ID NO 8
<211> LENGTH: 60
<212> TYPE: DNA
<213> ORGANISM: Artificial Sequence
<220> FEATURE:
<223> OTHER INFORMATION: Description of Artificial Sequence:Artificially
      Synthesized Oligonucleotide Sequence

<400> SEQUENCE: 8
gtagccgttg ctaccctcgt tccgatgctg tctttcgctg ctgagggtga cgatcccgca        60

<210> SEQ ID NO 9
<211> LENGTH: 60
<212> TYPE: DNA
<213> ORGANISM: Artificial Sequence
<220> FEATURE:
<223> OTHER INFORMATION: Description of Artificial Sequence:Artificially
      Synthesized Oligonucleotide Sequence

<400> SEQUENCE: 9
caaagcctct gtagccgttg ctaccctcgt tccgatgctg tctttcgctg ctgagggtga        60

<210> SEQ ID NO 10
<211> LENGTH: 60
<212> TYPE: DNA
<213> ORGANISM: Artificial Sequence
<220> FEATURE:
<223> OTHER INFORMATION: Description of Artificial Sequence:Artificially
      Synthesized Oligonucleotide Sequence

<400> SEQUENCE: 10
ctttagtcct caaagcctct gtagccgttg ctaccctcgt tccgatgctg tctttcgctg        60

<210> SEQ ID NO 11
<211> LENGTH: 80
<212> TYPE: DNA
<213> ORGANISM: Artificial Sequence
<220> FEATURE:
<223> OTHER INFORMATION: Description of Artificial Sequence:Artificially
      Synthesized Oligonucleotide Sequence

<400> SEQUENCE: 11

```
ctaccctcgt tccgatgctg tctttcgctg ctgagggtga cgatcccgca aaagcggcct    60
ttaactccct gcaagcctca                                                80
```

<210> SEQ ID NO 12
<211> LENGTH: 50
<212> TYPE: DNA
<213> ORGANISM: Artificial Sequence
<220> FEATURE:
<223> OTHER INFORMATION: Description of Artificial Sequence:Artificially
      Synthesized Oligonucleotide Sequence

<400> SEQUENCE: 12

```
ctgagggtga cgatcccgca aaagcggcct ttaactccct gcaagcctca               50
```

<210> SEQ ID NO 13
<211> LENGTH: 40
<212> TYPE: DNA
<213> ORGANISM: Artificial Sequence
<220> FEATURE:
<223> OTHER INFORMATION: Description of Artificial Sequence:Artificially
      Synthesized Oligonucleotide Sequence

<400> SEQUENCE: 13

```
cgatcccgca aaagcggcct ttaactccct gcaagcctca                          40
```

<210> SEQ ID NO 14
<211> LENGTH: 30
<212> TYPE: DNA
<213> ORGANISM: Artificial Sequence
<220> FEATURE:
<223> OTHER INFORMATION: Description of Artificial Sequence:Artificially
      Synthesized Oligonucleotide Sequence

<400> SEQUENCE: 14

```
aaagcggcct ttaactccct gcaagcctca                                     30
```

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence:Artificially
      Synthesized Oligonucleotide Sequence

<400> SEQUENCE: 15

```
ttaactccct gcaagcctca                                                20
```

<210> SEQ ID NO 16
<211> LENGTH: 60
<212> TYPE: DNA
<213> ORGANISM: Artificial Sequence
<220> FEATURE:
<223> OTHER INFORMATION: Description of Artificial Sequence:Artificially
      Synthesized Oligonucleotide Sequence

<400> SEQUENCE: 16

```
agaggctttg aggactaaag acttttcat caggaagttt ccattaaacg ggtaaaatac     60
```

<210> SEQ ID NO 17
<211> LENGTH: 60
<212> TYPE: DNA
<213> ORGANISM: Artificial Sequence
<220> FEATURE:
<223> OTHER INFORMATION: Description of Artificial Sequence:Artificially
      Synthesized Oligonucleotide Sequence

<400> SEQUENCE: 17
acgccgggca agagcaactc ggtcgccgca gacactattc tcagaatgac ttggttgagt        60

<210> SEQ ID NO 18
<211> LENGTH: 60
<212> TYPE: DNA
<213> ORGANISM: Artificial Sequence
<220> FEATURE:
<223> OTHER INFORMATION: Description of Artificial Sequence:Artificially
      Synthesized Oligonucleotide Sequence

<400> SEQUENCE: 18
acgccgggca agagcaactc ggtcgccgca aacactattc tcagaatgac ttggttgagt        60

<210> SEQ ID NO 19
<211> LENGTH: 60
<212> TYPE: DNA
<213> ORGANISM: Artificial Sequence
<220> FEATURE:
<223> OTHER INFORMATION: Description of Artificial Sequence:Artificially
      Synthesized Oligonucleotide Sequence

<400> SEQUENCE: 19
acgccgggca agagcaactc ggtcgccgca cacactattc tcagaatgac ttggttgagt        60

<210> SEQ ID NO 20
<211> LENGTH: 120
<212> TYPE: DNA
<213> ORGANISM: Artificial Sequence
<220> FEATURE:
<223> OTHER INFORMATION: Description of Artificial Sequence:Artificially
      Synthesized Oligonucleotide Sequence

<400> SEQUENCE: 20
tgcgggatcg tcaccctcag cagcgaaaga cagcatcgga acgagggtag caacggctac        60
agaggctttg aggactaaag acttttcat gaggaagttt ccattaaacg ggtaaaatac        120

<210> SEQ ID NO 21
<211> LENGTH: 120
<212> TYPE: DNA
<213> ORGANISM: Artificial Sequence
<220> FEATURE:
<223> OTHER INFORMATION: Description of Artificial Sequence:Artificially
      Synthesized Oligonucleotide Sequence

<400> SEQUENCE: 21
ggcgggatcg tcaccctcag cagcgaaaga cagcatcgga acgagggtag caacggctac        60
agaggctttg aggactaaag acttttcat gaggaagttt ccattaaacg ggtaaaatac        120

<210> SEQ ID NO 22
<211> LENGTH: 120
<212> TYPE: DNA
<213> ORGANISM: Artificial Sequence
<220> FEATURE:
<223> OTHER INFORMATION: Description of Artificial Sequence:Artificially
      Synthesized Oligonucleotide Sequence

<400> SEQUENCE: 22
tgcgggatcg tcacgctcag cagcgaaaga cagcatcgga acgagggtag caacggctac        60
agaggctttg aggactaaag acttttcat gaggaagttt ccattaaacg ggtaaaatac        120

<210> SEQ ID NO 23
<211> LENGTH: 120
<212> TYPE: DNA
<213> ORGANISM: Artificial Sequence

```
<220> FEATURE:
<223> OTHER INFORMATION: Description of Artificial Sequence:Artificially
      Synthesized Oligonucleotide Sequence

<400> SEQUENCE: 23
tgcgggatcg tcaccctcag cagcggaaga cagcatcgga acgagggtag caacggctac      60
agaggctttg aggactaaag acttttcat gaggaagttt ccattaaacg ggtaaaatac      120

<210> SEQ ID NO 24
<211> LENGTH: 120
<212> TYPE: DNA
<213> ORGANISM: Artificial Sequence
<220> FEATURE:
<223> OTHER INFORMATION: Description of Artificial Sequence:Artificially
      Synthesized Oligonucleotide Sequence

<400> SEQUENCE: 24
tgcgggatcg tcaccctcag cagcgaaaga cagcgtcgga acgagggtag caacggctac      60
agaggctttg aggactaaag acttttcat gaggaagttt ccattaaacg ggtaaaatac      120

<210> SEQ ID NO 25
<211> LENGTH: 120
<212> TYPE: DNA
<213> ORGANISM: Artificial Sequence
<220> FEATURE:
<223> OTHER INFORMATION: Description of Artificial Sequence:Artificially
      Synthesized Oligonucleotide Sequence

<400> SEQUENCE: 25
tgcgggatcg tcaccctcag cagcgaaaga cagcatcgga acgagggtag gaacggctac      60
agaggctttg aggactaaag acttttcat gaggaagttt ccattaaacg ggtaaaatac      120

<210> SEQ ID NO 26
<211> LENGTH: 119
<212> TYPE: DNA
<213> ORGANISM: Artificial Sequence
<220> FEATURE:
<223> OTHER INFORMATION: Description of Artificial Sequence:Artificially
      Synthesized Oligonucleotide Sequence

<400> SEQUENCE: 26
tgcgggatcg tcaccctcag cagcgaaaga cagcatcgga acgagggtag caacggtaca      60
gaggctgtga ggactaaaga cttttcatg aggaagtttc cattaaacgg gtaaaatac       119

<210> SEQ ID NO 27
<211> LENGTH: 120
<212> TYPE: DNA
<213> ORGANISM: Artificial Sequence
<220> FEATURE:
<223> OTHER INFORMATION: Description of Artificial Sequence:Artificially
      Synthesized Oligonucleotide Sequence

<400> SEQUENCE: 27
tgcgggatcg tcaccctcag cagcgaaaga cagcatcgga acgagggtag caacggctac      60
agaggctttg aggactaaag actttgtcat gaggaagttt ccattaaacg ggtaaaatac      120

<210> SEQ ID NO 28
<211> LENGTH: 120
<212> TYPE: DNA
<213> ORGANISM: Artificial Sequence
<220> FEATURE:
<223> OTHER INFORMATION: Description of Artificial Sequence:Artificially
      Synthesized Oligonucleotide Sequence
```

```
<400> SEQUENCE: 28
tgcgggatcg tcaccctcag cagcgaaaga cagcatcgga acgagggtag caacggctac      60
agaggctttg aggactaaag acttttcat gaggaggttt ccattaaacg ggtaaaatac      120

<210> SEQ ID NO 29
<211> LENGTH: 120
<212> TYPE: DNA
<213> ORGANISM: Artificial Sequence
<220> FEATURE:
<223> OTHER INFORMATION: Description of Artificial Sequence:Artificially
      Synthesized Oligonucleotide Sequence
<400> SEQUENCE: 29
tgcgggatcg tcaccctcag cagcgaaaga cagcatcgga acgagggtag caacggctac      60
agaggctttg aggactaaag acttttcat gaggaagttt ccattgaacg ggtaaaatac      120

<210> SEQ ID NO 30
<211> LENGTH: 60
<212> TYPE: DNA
<213> ORGANISM: Artificial Sequence
<220> FEATURE:
<223> OTHER INFORMATION: Description of Artificial Sequence:Artificially
      Synthesized Oligonucleotide Sequence

<400> SEQUENCE: 30
cgaggctttg aggactaaag acttttcat gaggaagttt ccattaaacg ggtaaaatac       60

<210> SEQ ID NO 31
<211> LENGTH: 60
<212> TYPE: DNA
<213> ORGANISM: Artificial Sequence
<220> FEATURE:
<223> OTHER INFORMATION: Description of Artificial Sequence:Artificially
      Synthesized Oligonucleotide Sequence

<400> SEQUENCE: 31
agaggctttg cggactaaag acttttcat gaggaagttt ccattaaacg ggtaaaatac       60

<210> SEQ ID NO 32
<211> LENGTH: 60
<212> TYPE: DNA
<213> ORGANISM: Artificial Sequence
<220> FEATURE:
<223> OTHER INFORMATION: Description of Artificial Sequence:Artificially
      Synthesized Oligonucleotide Sequence

<400> SEQUENCE: 32
agaggctttg aggactaaag ccttttcat gaggaagttt ccattaaacg ggtaaaatac       60

<210> SEQ ID NO 33
<211> LENGTH: 60
<212> TYPE: DNA
<213> ORGANISM: Artificial Sequence
<220> FEATURE:
<223> OTHER INFORMATION: Description of Artificial Sequence:Artificially
      Synthesized Oligonucleotide Sequence

<400> SEQUENCE: 33
agaggctttg aggactaaag acttttcat gaggaagttc ccattaaacg ggtaaaatac       60

<210> SEQ ID NO 34
<211> LENGTH: 60
<212> TYPE: DNA
<213> ORGANISM: Artificial Sequence
<220> FEATURE:
<223> OTHER INFORMATION: Description of Artificial Sequence:Artificially
```

-continued

```
       Synthesized Oligonucleotide Sequence

<400> SEQUENCE: 34
agaggctttg aggactaaag acttttcat gaggaagttt ccattaaacc ggtaaaatac    60

<210> SEQ ID NO 35
<211> LENGTH: 60
<212> TYPE: DNA
<213> ORGANISM: Artificial Sequence
<220> FEATURE:
<223> OTHER INFORMATION: Description of Artificial Sequence:Artificially
      Synthesized Oligonucleotide Sequence

<400> SEQUENCE: 35
agaggctttg aggactaaag acttttcat gaggaagttt ccattaaacg ggtaaaatcc    60

<210> SEQ ID NO 36
<211> LENGTH: 61
<212> TYPE: DNA
<213> ORGANISM: Artificial Sequence
<220> FEATURE:
<223> OTHER INFORMATION: Description of Artificial Sequence:Artificially
      Synthesized Oligonucleotide Sequence

<400> SEQUENCE: 36
agaggctttg aggactaaag actttttcat gcaggaagtt tccattaaac gggtaaaata    60
c                                                                   61

<210> SEQ ID NO 37
<211> LENGTH: 59
<212> TYPE: DNA
<213> ORGANISM: Artificial Sequence
<220> FEATURE:
<223> OTHER INFORMATION: Description of Artificial Sequence:Artificially
      Synthesized Oligonucleotide Sequence

<400> SEQUENCE: 37
agaggctttg aggactaaag actttttcat aggaagtttc cattaaacgg gtaaaatac    59
```